US009803192B2

(12) United States Patent  
Craighead et al.

(10) Patent No.: US 9,803,192 B2  
(45) Date of Patent: Oct. 31, 2017

(54) PROGRAMMABLE AND RECONFIGURABLE MICROCOLUMN AFFINITY CHROMATOGRAPHY DEVICE, SYSTEM, AND METHODS OF USE THEREOF

(71) Applicant: CORNELL UNIVERSITY, Ithaca, NY (US)

(72) Inventors: Harold G. Craighead, Ithaca, NY (US); Kylan Szeto, Ithaca, NY (US); Sarah Reinholt, Ithaca, NY (US); John T. Lis, Ithaca, NY (US); Abdullah Ozer, Vestal, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 66 days.

(21) Appl. No.: 14/507,819

(22) Filed: Oct. 6, 2014

(65) Prior Publication Data

US 2015/0166987 A1 Jun. 18, 2015

Related U.S. Application Data

(60) Provisional application No. 61/886,774, filed on Oct. 4, 2013.

(51) Int. Cl.
*C12N 15/10* (2006.01)
*B01D 15/38* (2006.01)
*B01D 15/22* (2006.01)

(52) U.S. Cl.
CPC ......... *C12N 15/1048* (2013.01); *B01D 15/22* (2013.01); *B01D 15/3819* (2013.01); *C12N 15/101* (2013.01)

(58) Field of Classification Search
CPC .................................................. B01D 2265/06
See application file for complete search history.

(56) References Cited

U.S. PATENT DOCUMENTS 4,510,058 A * 4/1985 Cais ................... B01D 15/1892
    210/198.2
6,054,047 A * 4/2000 Hindsgaul ............ G01N 30/466
    210/143

(Continued)

FOREIGN PATENT DOCUMENTS

EP     0 968 057     *  1/1998
EP     1 163 052     *  8/2000

(Continued)

OTHER PUBLICATIONS

Dufau et al, J. Biol. Chem. 250(12): 4822-4824, 1975.*

(Continued)

*Primary Examiner* — Kevin Hill
(74) *Attorney, Agent, or Firm* — FisherBroyles, LLP; Andrew K. Gonsalves, Esq.

(57) ABSTRACT

The present invention generally relates to microcolumn affinity chromatography devices, systems that include the microcolumn affinity chromatography devices of the present disclosure, methods of using the devices and the systems of the present disclosure, and methods of making the devices and the systems of the present disclosure. In certain embodiments, the microcolumn affinity chromatography device is suitable for conducting affinity chromatography in multiple microcolumns in parallel and/or in series.

38 Claims, 33 Drawing Sheets

(56) References Cited

U.S. PATENT DOCUMENTS

| | | | |
|---|---|---|---|
| 6,566,461 B2 | 5/2003 | Freitag et al. | |
| 7,981,362 B2 | 7/2011 | Glezer et al. | |
| 8,124,064 B2 | 2/2012 | Wei et al. | |
| 8,590,567 B2 | 11/2013 | Wilke et al. | |
| 2003/0049862 A1* | 3/2003 | He | B01L 3/5025 506/16 |
| 2003/0099954 A1* | 5/2003 | Miltenyi | B03C 1/002 435/6.11 |
| 2004/0109793 A1 | 6/2004 | McNeely et al. | |

FOREIGN PATENT DOCUMENTS

| | | |
|---|---|---|
| EP | 968057 B1 | 7/2003 |
| EP | 1864715 A1 | 12/2007 |
| EP | 1163052 B1 | 6/2010 |
| JP | 2010508525 A | 3/2010 |

OTHER PUBLICATIONS

Phillips, Handbook of Affinity Chromatography, Chapter 28: 763-787, Taylor & Francis Group ed, 2006.*
Ellington et al, Nature 346:818-822, 1990.*
Cox et al, Biotechnol. Prog. 14:845-850, 1998.*
Mirsky et al, J. Lab. Automation 17(2):116-124; available online Jan. 24, 2012.*
Yang et al, Anal. Chem. 81:5484-5489, 2009.*

* cited by examiner

Microcolumn Device

Microcolumn Device with Top and Bottom Frit Gasket Layers

Serial Assembly with Top and Bottom Channel Layers

Serial Assembly with Top and Bottom Channel Layers, and Top Port Layer

Serial Assembly with Top and Bottom Channel Layers, Top Port Layer, and Top and Bottom Frit Gasket Layers Serial Assembly with Top and Bottom Channel Layers, Top Port Layer,
Top and Bottom Frit Gasket Layers, and Top Washer Layer Serial Assembly with Top and Bottom Channel Layers, Top Port Layer,
Top and Bottom Frit Gasket Layers, Top Washer Layer, and Bottom Support Layer Parallel Assembly with Top and Bottom Port Layers Parallel Assembly with Top and Bottom Port Layers, and with Top and Bottom Washer Layers Parallel Assembly with Top and Bottom Port Layers, Top and Bottom Washer Layers, and Top and Bottom Frit Gasket Layers

First test: Plate Layout

|  | SERIAL | [GFP] (II) | [HSF] (II) | [NeIf-E] (II) |
|---|---|---|---|---|
| 1. Empty | | | | |
| 2. Glutathione | | | | |
| 3. Nickel-NTA | | | | |
| 4. Amylose | | | | |
| 5. GFP | | | | |
| 6. HSF | | | | |
| 7. NeIf-E | | | | |
| 8. UBLCP1 | | | | |

- Every Test performed in triplicate to test reproducibility

Figure 20

SEQUENCE LISTING

<160> NUMBER OF SEQ ID NOS: 15

<210> SEQ ID NO 1
<211> LENGTH: 84
<212> TYPE: RNA
<213> ORGANISM: Artificial Sequence
<220> FEATURE:
<223> OTHER INFORMATION: Synthetic Aptamer

<400> SEQUENCE: 1
agcuucugga cugcgauggg agcacgaaac gucguggcgc aauugggugg ggaaaguccu    60
uaaaagaggg ccaccacaga agcu                                          84

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gcttctggac tgcgatggga gca                                    23

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
gcttctgtgg tggccctctt ttaaggact                              29

<210> SEQ ID NO 4
<211> LENGTH: 117
<212> TYPE: RNA
<213> ORGANISM: Artificial Sequence
<220> FEATURE:
<223> OTHER INFORMATION: Synthetic Aptamer

<400> SEQUENCE: 4
gggaauggau ccacaucuac gaauucaauc aaguccccag acucagcaac acuggacagc    60
gauaugcaga uaaccaagac caauucacuc caguucacug cagacuugac gaagcuu      117

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
ctggagtgaa ttggtcttgg ttatc                                  25

<210> SEQ ID NO 6
<211> LENGTH: 120
<212> TYPE: RNA
<213> ORGANISM: Artificial Sequence
<220> FEATURE:
<223> OTHER INFORMATION: Synthetic Aptamer

<400> SEQUENCE: 6
gggaauggau ccacaucuac gaauucccaa cgacugccga gcgagauuac gcuugagcgc    60
cccacugagg augcccacgg gcgauugggg cacggcuuca cugcagacuu gacgaagcuu   120

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gccgtgcccc aatcgcccgt g                                      21

<210> SEQ ID NO 8
<211> LENGTH: 118
<212> TYPE: RNA
<213> ORGANISM: Artificial Sequence
<220> FEATURE:
<223> OTHER INFORMATION: Synthetic Aptamer

```
<400> SEQUENCE: 8
gggaauggau ccacaucuac gaauuccgca gggcuagccg caugcucagg ccuggcgggu    60
agggaguuag gguagggaga ccaggagagc uggcuucacu gcagacuuga cgaagcuu    118

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
cgcagggcta gccgcatg                                                 18

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
gccagctctc ctggtctcc                                                19

<210> SEQ ID NO 11
<211> LENGTH: 121
<212> TYPE: RNA
<213> ORGANISM: Artificial Sequence
<220> FEATURE:
<223> OTHER INFORMATION: Synthetic Aptamer

<400> SEQUENCE: 11
gggaauggau ccacaucuac gaauuccgaa gcucgugacg guaccuccua aaauguccau    60
ggggaaggga gggaauggga aggacaaucg gacaccguuc acugcagacu ugacgaagcu   120
u                                                                   121

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
cgaagctcgt gacggtacc                                                19

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
cggtgtccga ttgtccttc                                                19

<210> SEQ ID NO 14
<211> LENGTH: 41
<212> TYPE: DNA
<213> ORGANISM: Artificial Sequence
<220> FEATURE:
<223> OTHER INFORMATION: Primer
```

-continued

```
<400> SEQUENCE: 14
gataatacga ctcactatag ggaatggatc cacatctacg a                          41

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
aagcttcgtc aagtctgcag tgaa                                             24
```

PROGRAMMABLE AND RECONFIGURABLE MICROCOLUMN AFFINITY CHROMATOGRAPHY DEVICE, SYSTEM, AND METHODS OF USE THEREOF

CROSS-REFERENCE TO RELATED APPLICATIONS

This application claims priority benefit of U.S. Provisional Patent Application Ser. No. 61/886,774, filed Oct. 4, 2013, the disclosure of which is hereby incorporated by reference herein in its entirety.

GOVERNMENT RIGHTS STATEMENT

This invention was made with Government support under grant number R01-GM090320-01 awarded by the National Institutes of Health. The United States Government has certain rights in the invention.

FIELD OF THE INVENTION

The present invention generally relates to a microcolumn affinity chromatography device, a system that includes the microcolumn affinity chromatography device, methods of using the device and the system, and methods of making the device and the system.

BACKGROUND OF THE INVENTION

SELEX (Systematic Evolution of Ligands by EXponential enrichment) is an in vitro selection method used to generate high affinity ligands for specific target compounds (Ellington A D, Szostak J W (1990) Invitro Selection of Rna Molecules That Bind Specific Ligands. Nature 346 (6287): 818-822; Joyce G F (1989) Amplification, mutation and selection of catalytic RNA. Gene 82 (1):83-87; Tuerk C, Gold L (1990) Systematic evolution of ligands by exponential enrichment: RNA ligands to bacteriophage T4 DNA polymerase. Science 249 (4968):505-510). These selected molecules, called aptamers, are derived from large libraries of nucleic acids with random sequences through an iterative process of binding, partitioning, and amplification of sequences that bind to the target. This process enriches the initial random library for higher binding affinity sequences, and the cycle is repeated until the molecules in the enriched pools converge on the highest affinity sequence. Since this method was first introduced, aptamers have become valuable tools in biotechnology, diagnostics and therapeutics (Tombelli S, Mascini M (2009) Aptamers as molecular tools for bioanalytical methods. Current opinion in molecular therapeutics 11 (2):179-188).

There is interest in improving SELEX technology to obtain highly specific aptamers much more rapidly. However, despite their potential, many technologies are difficult to scale for multiplexed or parallel selections. For example, Park et al. and Ahn et al. used microfluidic sol-gel devices that could utilize up to five targets for multiplexing (Park S M, Ahn J Y, Jo M, Lee D K, Lis J T, Craighead H G, Kim S (2009) Selection and elution of aptamers using nanoporous sol-gel arrays with integrated microheaters. Lab on a chip 9 (9):1206-1212; Ahn J Y, Jo M, Dua P, Lee D K, Kim S (2011) A sol-gel-based microfluidics system enhances the efficiency of RNA aptamer selection. Oligonucleotides 21 (2):93-100), but currently no large-scale microfluidic selections have been demonstrated. Large-scale parallel selections have been done with microplate technologies, which are of particular interest due to the availability of protocols and automated liquid handling devices (Cox J C, Ellington A D (2001) Automated selection of anti-protein aptamers. Bioorganic & medicinal chemistry 9 (10):2525-2531; Cox J C, Rudolph P, Ellington A D (1998) Automated RNA selection. Biotechnology progress 14 (6):845-850). However, in contrast to microfluidic devices that utilize flow and other dynamic behavior, most of these selections rely on traditional equilibrium solution binding (Eulberg D, Buchner K, Maasch C, Klussmann S (2005) Development of an automated in vitro selection protocol to obtain RNA-based aptamers: identification of a biostable substance P antagonist. Nucleic Acids Res 33 (4):e45) or interactions with target molecules that are bound or adsorbed to the plate surface (Drolet D W, Jenison R D, Smith D E, Pratt D, Hicke B J (1999) A high throughput platform for systematic evolution of ligands by exponential enrichment (SELEX). Combinatorial chemistry & high throughput screening 2 (5):271-278; Jolma A, Kivioja T, Toivonen J, Cheng L, Wei G, Enge M, Taipale M, Vaquerizas J M, Yan J, Sillanpaa M J, Bonke M, Palin K, Talukder S, Hughes T R, Luscombe N M, Ukkonen E, Taipale J (2010) Multiplexed massively parallel SELEX for characterization of human transcription factor binding specificities. Genome research 20 (6):861-873).

Despite advances toward more sophisticated and automated SELEX, little has been done to characterize and optimize new or current technologies, and recent binding studies show significant discrepancies with existing theory (Daniel C, Roupioz Y, Gasparutto D, Livache T, Buhot A (2013) Solution-Phase vs Surface-Phase Aptamer-Protein Affinity from a Label-Free Kinetic Biosensor. PloS one 8 (9):e75419; Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85 (6):3417-3424). Therefore, empirical methods have been used to optimize selection conditions and aid the development of new models (Ozer A, White B S, Lis J T, Shalloway D (2013) Density-dependent cooperative nonspecific binding in solid-phase SELEX affinity selection. Nucleic Acids Res 41 (14):7167-7175). As new high-throughput technologies emerge, these studies will become even more important in order to obtain the most effective and robust selections under the available parameters.

The present invention is directed to overcoming these and other deficiencies in the art.

SUMMARY OF THE INVENTION

The present invention generally relates to microcolumn affinity chromatography devices, systems that include the microcolumn affinity chromatography devices of the present disclosure, methods of using the devices and the systems of the present disclosure, and methods of making the devices and the systems of the present disclosure.

In one aspect, the present invention relates to a device for conducting affinity chromatography in multiple microcolumns in parallel and/or in series. In one embodiment, the device comprises: (i) a microcolumn layer comprising a top surface, a bottom surface, and a plurality of substantially vertically aligned microcolumns for passing one or more sample liquids therethrough, said microcolumns extending from the top to the bottom surface of the microcolumn layer and optionally containing an affinity chromatography agent; (ii) a top capping layer proximately disposed at the top surface of the microcolumn layer and comprising a patterned grid having at least one opening in fluid alignment with at least one microcolumn so as to allow a sample liquid to pass through the top capping layer and into the microcolumn; and (iii) a bottom capping layer proximately disposed at the bottom surface of the microcolumn layer and comprising either a parallel patterned grid for running multiple liquid samples through the microcolumns in a parallel manner or a series patterned grid for passing a single liquid sample through multiple serially connected microcolumns in a serial manner.

In another aspect, the present invention relates to a system for collecting one or more liquid sample from an affinity chromatography microcolumn device. In one embodiment, the system comprises: (i) a device for conducting affinity chromatography in multiple microcolumns in parallel and/or in series, as provided herein; (ii) a liquid flow mechanism for moving a liquid sample into, through, and out of a microcolumn; and (iii) a liquid collection apparatus comprising well portions for collecting liquid samples from the microcolumns, where each well portion is aligned with a single corresponding microcolumn for collection of the liquid sample therefrom.

In yet another aspect, the present invention relates to a method of collecting one or more liquid sample from an affinity chromatography microcolumn for further analysis. In one embodiment, this method comprises: (i) providing a system for collecting one or more liquid sample from an affinity chromatography microcolumn device, as provided herein; (ii) running one or more liquid sample through the microcolumns of the device of the system either in a parallel manner or a serial manner under conditions effective to allow a test agent contained in the liquid sample to bind specifically to a target molecule contained in the microcolumn of the device; and (iii) recovering from each microcolumn the test agent or test agents that bind specifically to the respective target molecules of each microcolumn device, said recovering taking place in the liquid collection apparatus.

The devices and systems of the present disclosure are useful for a variety of applications. In a particular application, the devices and systems of the present disclosure are useful for aptamer selection. As is understood in the field, aptamer selections are often tedious and not easily scalable, and the selection process is typically far from optimal, as few studies have been done to characterize and optimize it. In one aspect, the present disclosure provides a high-throughput device designed for efficient, large-scale aptamer selections, as well as for characterization and optimization of the selection process. In certain embodiments, this device includes, without limitation, 96 microcolumns arranged within a single device with the same dimensions as a 96-well microplate, allowing it to be coupled directly to a microplate. The general technology of the present invention is sometimes referred to herein as MEDUSA (Microplate-based Enrichment Device Used for the Selection of Aptamers), and generally is a layered device that is easily customizable and reconfigurable using a customizable fabrication technique. In certain embodiments, a $CO_2$ laser can be used to cut the different layers precisely. One advantage of MEDUSA is that it can be assembled such that the microcolumns are connected in series or in parallel.

Embodiments of the MEDUSA device of the present disclosure have been used to characterize aspects of RNA aptamer selections; namely, the effect of resin-immobilized protein target concentration on aptamer binding efficiency, the selectivity and partitioning efficiency of three RNA aptamers to their respective targets and non-specific surfaces, and the binding of background binding sequences to the same targets and surfaces. A smaller customized version of MEDUSA using fewer microcolumns, but keeping the microplate-based layout, was used to perform RNA aptamer selections to 12 different protein targets with a single aliquot of library using MEDUSA connected in series for the initial binding step, and parallel mode for the successive steps. In this selection, all steps were performed using microplate-based methods to demonstrate the potential for automation of the selection process using MEDUSA. The plate-based format allows easy integration with other plate-based systems for downstream biochemical processes and analysis, and this enables MEDUSA to be used for large-scale, high-throughput aptamer selections, as well as characterization and optimization of the aptamer selection process.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 20 is a graph illustrating results of an experiment using a microcolumn device of the present disclosure in both serial and parallel selections simultaneously.

FIG. 38A: An exploded view of the customized device layers for configuring all 96 microcolumns to run in parallel. The flow path is shown in the lower boxed inset with no connections between microcolumns. The layers numbered 1 to 3 are the plastic layers: the middle layer (1) containing the microcolumns, the next outer two layers being the caps (2) and washers (3). The outermost layers (4) consist of inlet and outlet ports that are bonded to the final device. The two layers numbered (5) are silicone layers, which are bonded to the microcolumn layer (1) to hold porous frits against both sides of the microcolumns to retain affinity resin and to make liquid-tight seals across the entire device. A photograph of MEDUSA assembled in parallel is shown in the upper inset. FIG. 38B: The customized device layers for configuring 24 of the microcolumns to run in series. The two additional silicone layers (6) shown in blue, as well as the smaller complementary plastic layers (2 and 3) on the left, are specifically programmed to connect 3 sets of 8 microcolumns within the device. The flow path is shown in the lower boxed inset with microcolumns connected in series via a serpentine route through 8 microcolumns. MEDUSA assembled to run in series and parallel is shown in the upper inset.

FIG. 39A: The recovery of GFPapt and N70 library at various concentrations of GFP. Analogous data for the recovery of (FIG. 39B) HSFapt and N70 library from hHSF1, and (FIG. 39C) NELFapt and N70 library from NELF-E. FIGS. 39D-39F: The calculated enrichments of the specific aptamers (GFPapt, HSFapt, NELFapt) over the random library. The error bars represent the standard deviation in recoveries or enrichments calculated for each condition performed in triplicate.

DETAILED DESCRIPTION OF THE INVENTION

Figure 1A:
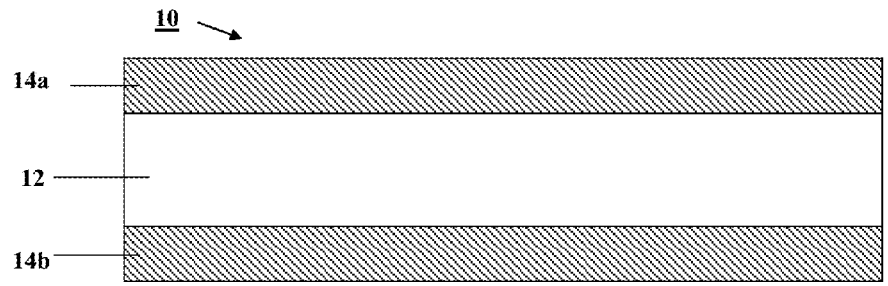
FIGS. 1A-1B are schematics illustrating the layers of embodiments of a microcolumn device of the present disclosure.

The present disclosure generally relates to, inter alia, microcolumn affinity chromatography devices, systems that include the microcolumn affinity chromatography devices of the present disclosure, methods of using the devices and the systems of the present disclosure, and methods of making the devices and the systems of the present disclosure. One advantage of the microcolumn affinity chromatography device of the present disclosure is that it can be programmed and reconfigured in order to allow, inter alia, high-throughput analyses for various applications, including, without limitation, aptamer selection applications.

In one aspect, the present disclosure provides a device for conducting affinity chromatography. In a particular, the present disclosure provides a device for conducting affinity chromatography using microcolumns. More particularly, the present disclosure provides a device for conducting affinity chromatography in multiple microcolumns in parallel and/or in series. The various embodiments of the devices of the present disclosure are programmable and reconfigurable, as described in more detail herein.

In one embodiment, the device of the present disclosure comprises: a microcolumn layer; a top capping layer; and a bottom capping layer. The microcolumn layer comprises a top surface, a bottom surface, and a plurality of substantially vertically aligned microcolumns for passing one or more sample liquids therethrough. The microcolumns extend from the top to the bottom surface of the microcolumn layer and optionally contain an affinity chromatography agent. The top capping layer is proximately disposed at the top surface of the microcolumn layer and comprises a patterned grid having at least one opening in fluid alignment with at least one microcolumn so as to allow a sample liquid to pass through the top capping layer and into the microcolumn. The bottom capping layer is proximately disposed at the bottom surface of the microcolumn layer and comprises either a parallel patterned grid for running multiple liquid samples through the microcolumns in a parallel manner or a series patterned grid for passing a single liquid sample through multiple serially connected microcolumns in a serial manner.

The microcolumn layer can be made of various materials suitable for use as described herein. Examples of suitable materials for the microcolumn layer include, without limitation, poly(methyl methacrylate) (PMMA), cyclic olefin copolymer, polyethylene, polypropylene, and polystyrene, or functional derivatives or variants thereof.

Similarly, the top capping layer and the bottom capping layer can be made of a material that includes, but is not limited to, poly(methyl methacrylate) (PMMA), cyclic olefin copolymer, polyethylene, polypropylene, and polystyrene, or functional derivatives or variants thereof.

The parallel patterned grid of the bottom capping layer comprises opening portions in fluid alignment with those microcolumns through which liquid samples are desired to pass in a parallel manner.

The series patterned grid of the bottom capping layer can further includes a bottom channel layer having a plurality of substantially horizontal channel portions, each forming a flow channel fluidly connecting adjacent microcolumns of the serially connected microcolumns through which the single liquid sample is desired to pass in a serial manner.

In one embodiment, the device can further include a top channel layer disposed between the top capping layer and the top surface of the microcolumn layer. In such an embodiment, the top channel layer can include a plurality of substantially horizontal channel portions, each forming a flow channel fluidly connecting adjacent microcolumns of the serially connected microcolumns through which the single liquid sample is desired to pass in a serial manner.

In a particular embodiment, the top channel layer is patterned to work in fluid and serial connection with the plurality of horizontal channel portions of the bottom capping layer so as to pass the single liquid sample through the serially connected microcolumns in a serial manner.

The top channel layer can be made of any material suitable for allowing the top channel layer to function as described herein. Examples of suitable materials for use as the top channel layer include, without limitation, silicone, rubber, or any functional derivatives or variants thereof.

In one embodiment, the device of the present disclosure further comprises a top port layer proximately disposed on the top capping layer. The top port layer comprises one or more input port, each in fluidic alignment with a corresponding microcolumn so as to effectuate introduction of a sample liquid into a desired microcolumn. In certain embodiments, the top port layer further comprises at least one outlet port for expelling a liquid sample from one of the microcolumns after it passes through a plurality of serially connected microcolumns in serial manner. As indicated, this sort of configuration is suitable for use in serial applications of the devise of the present disclosure.

In one embodiment, the device of the present disclosure can further comprise a bottom port layer proximately disposed on the bottom capping layer. The bottom port layer comprises one or more outlet port, each in fluidic alignment with a corresponding microcolumn so as to effectuate expulsion of a liquid sample from a desired microcolumn.

The ports of the top port layer and bottom port layer can include, without limitation, NanoPorts™, connectors, tubing, or the like, or any structure suitable for performing the port function as described herein. A suitable material for use in making the ports can include, for example, a polymer, a thermoplastic polymer, polyether ether ketone (PEEK), or functional derivatives or variants thereof.

In one embodiment, the device of the present disclosure further comprises a top frit gasket layer and/or a bottom frit gasket layer for aiding the containment of an affinity chromatography agent within the microcolumns. In such an embodiment, the top frit gasket layer is deposited between the top surface of the microcolumn layer and the top capping layer, and the bottom frit gasket layer is deposited between the bottom surface of the microcolumn layer and the bottom capping layer.

The top and bottom frit gasket layers can be made of various materials, particularly those materials suitable for use as gaskets, including, without limitation, materials such as silicone, rubber, plastic polymers (e.g., polychlorotrifluoroethylene), polytetrafluoroethylene (otherwise known as PTFE or Teflon), paper, metal, cork, felt, neoprene, nitrile rubber, and fiberglass, or functional derivatives or variants thereof.

In one embodiment, the device of the present disclosure further comprises: a top port layer; an optional bottom port layer; a top washer layer; and/or a bottom washer layer. The top port layer is proximately disposed on the top capping layer, with the top port layer comprising one or more input port, each in fluidic alignment with a corresponding microcolumn so as to effectuate introduction of a sample liquid into a desired microcolumn. The optional bottom port layer is proximately disposed on the bottom capping layer and comprises one or more outlet port, each in fluidic alignment with a corresponding microcolumn so as to effectuate expulsion of a liquid sample from a desired microcolumn. The top washer layer and/or the bottom washer layer is provided for securing the ports of the top port layer and the optional bottom port layer in alignment with their corresponding microcolumns. The top washer layer is proximately deposited at the top capping layer and comprises a plurality of openings through which the ports of the top port layer protrude. The bottom washer layer is proximately deposited at the bottom capping layer and comprises a plurality of openings through which the ports of the optional bottom port layer protrude.

The top and bottom washer layers can be made of various materials that are suitable for use as washers for the ports. Examples of suitable materials for the washers include, without limitation, poly(methyl methacrylate) (PMMA), cyclic olefin copolymer, polyethylene, polypropylene, polystyrene, or functional derivatives and variants thereof.

As described herein, the microcolumn layer includes a plurality of substantially vertically aligned microcolumns for passing one or more sample liquids therethrough, particularly to effectuate affinity chromatography in the microcolumns. The microcolumns are generally channels that allow for a certain volume of liquid and/or affinity chromatography agents to reside in the microcolumn at a given moment.

The microcolumns can be of the same or varying volume capacity and dimension. In various embodiments, the microcolumns can have a volume capacity of between about 0.5 μL and about 250 μL, between about 0.5 μL and about 225 μL, between about 0.5 μL and about 200 μL, between about 0.5 μL and about 175 μL, between about 0.5 μL and about 150 μL, between about 0.5 μL and 125 about μL, between about 0.5 μL and about 100 μL, between about 0.5 μL and about 90 μL, between about 0.5 μL and about 80 μL, between about 0.5 μL and about 70 μL, between about 0.5 μL and about 60 μL, between about 0.5 μL and about 50 μL, between about 0.5 μL and about 40 μL, between about 0.5 μL and about 35 μL, between about 0.5 μL and about 30 μL, between about 0.5 μL and about 25 μL, between about 0.5 μL and about 20 μL, between about 0.5 μL and about 15 μL, between about 0.5 μL and about 10 μL, between about 0.5 μL and about 5 μL, between about 0.5 μL and about 2.5 μL, between about 0.5 μL and about μL 2.0, between about 0.5 μL and about 1.5 μL, or between about 0.5 μL and about 1.0 μL.

As described herein, the microcolumns can optionally contain an affinity chromatography agent. Suitable affinity chromatography agents refer to any agent that is effective in aiding the affinity chromatography function of the microcolumn. Without intending to be limiting, examples of suitable affinity chromatography agents for the present disclosure can include, without limitation, a resin, a modified resin, microbeads, and the like.

In one embodiment, the affinity chromatography agent comprises an immobilized target molecule. In a particular embodiment, the immobilized target molecule is labeled. In certain embodiments, the immobilized target molecule can include, without limitation, a whole cell, a virus, a virus particle, a protein, a modified protein, a polypeptide, a modified polypeptide, an RNA molecule, a DNA molecule, a modified DNA molecule, a polysaccharide, an amino acid, an antibiotic, a pharmaceutical agent, an organic non-pharmaceutical agent, a macromolecular complex, a carbohydrate, a lipid, a small molecule, a chemical compound, a mixture of lysed cells, or a mixture of purified, partially purified, or non-purified protein.

In certain embodiments, the immobilized target molecule is provided from a mixture of lysed cells, a mixture of purified, partially purified, or non-purified protein.

As described herein, the device of the present disclosure is useful for conducting affinity chromatography in multiple microcolumns, either in parallel and/or in series. As used herein, the term "affinity chromatography" is meant to cover all affinity chromatography techniques that can take place in a microcolumn, as described herein. For example, as used herein, affinity chromatography can involve, without limitation, anion exchange technology, group exclusions, immobilized-metal affinity chromatography (IMAC), fusion tag protein purification, pull-down assays, and/or immunoprecipitations.

In accordance with the device of the present disclosure, the one or more liquid sample can comprise one or more test agent for running through at least one of the microcolumns to determine its affinity or lack of affinity to the affinity chromatography agent. The test agent can include, without limitation, an aptamer, a protein, a protein complex, a modified protein, a polypeptide, a modified polypeptide, an RNA molecule, a DNA molecule, a modified DNA molecule, a drug, as well as any other molecules or ligands of interest.

Various aspects and embodiments of the device of the present disclosure are further described by way of schematic illustrations in FIGS. 1A-1B, 2A-2E, 3A-3C, and 4A-4B. The schematic illustrations of FIGS. 1A-1B, 2A-2E, and 3A-3C are cross-sectional representations of various layers of embodiments of the device of the present disclosure. These cross-sectional representations are not meant to illustrate the exact structure of the layers, nor are they meant to illustrate the relative dimensions (e.g., widths or lengths) of each of the layers. Instead, these cross-sectional illustrations are meant to show the layers as they relate to one another in terms of placement (e.g., sometimes referred to as where they are deposited or disposed in relation to one another).

Turning now to FIG. 1A, device 10 is shown to include microcolumn layer 12, top capping layer 14a, and bottom capping layer 14b.

Figure 1B:
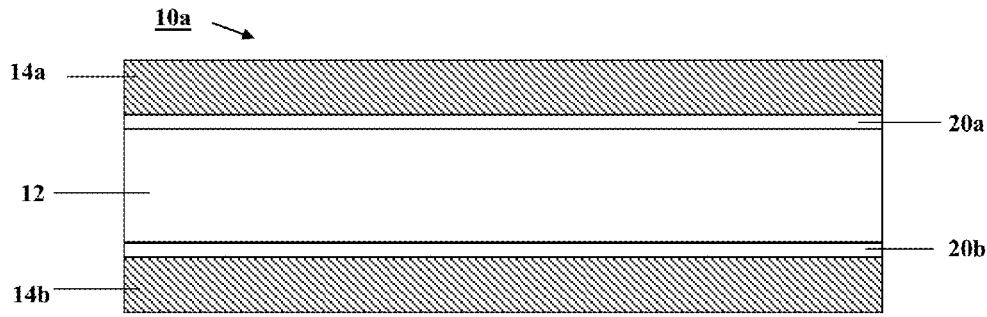

Turning now to FIG. 1B, device 10a is shown to include microcolumn layer 12, with top frit gasket layer 20a layered on top of microcolumn layer 12, and with top capping layer 14a layered on top of top frit gasket layer 20a. Bottom frit gasket layer 20b is disposed proximate to the bottom surface of microcolumn layer 12, and then bottom capping layer 14b is layered proximate to bottom capping layer 14b.

FIGS. 2A-2E are illustrations of various embodiments of the device of the present disclosure in serial assembly form.

Figure 2A:
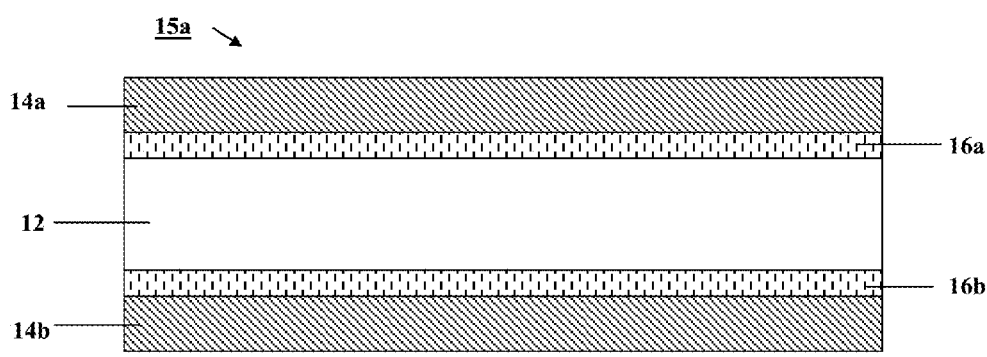
FIGS. 2A-2E are schematics illustrating the layers of embodiments of a microcolumn device of the present disclosure assembled for serial use.

Turning now to FIG. 2A, device 15a includes microcolumn layer 12 with top channel layer 16a disposed on the top surface of microcolumn layer 12, and then with top capping layer 14a disposed on top channel layer 16a. Bottom channel layer 16b is disposed on the bottom surface of microcolumn layer 12, and then bottom capping layer 14b is disposed on bottom channel layer 16b.

Figure 2B:
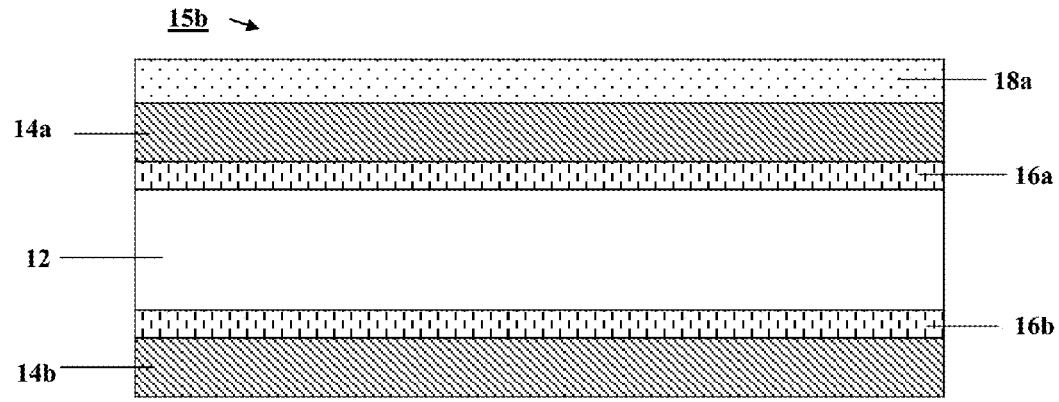

Turning now to FIG. 2B, device 15b includes microcolumn layer 12 with top channel layer 16a disposed on the top surface of microcolumn layer 12, top capping layer 14a disposed on top channel layer 16a, and top port layer 18a disposed on top capping layer 14a. Bottom channel layer 16b is disposed on the bottom surface of microcolumn layer 12, and then bottom capping layer 14b is disposed on bottom channel layer 16b.

Figure 2C:
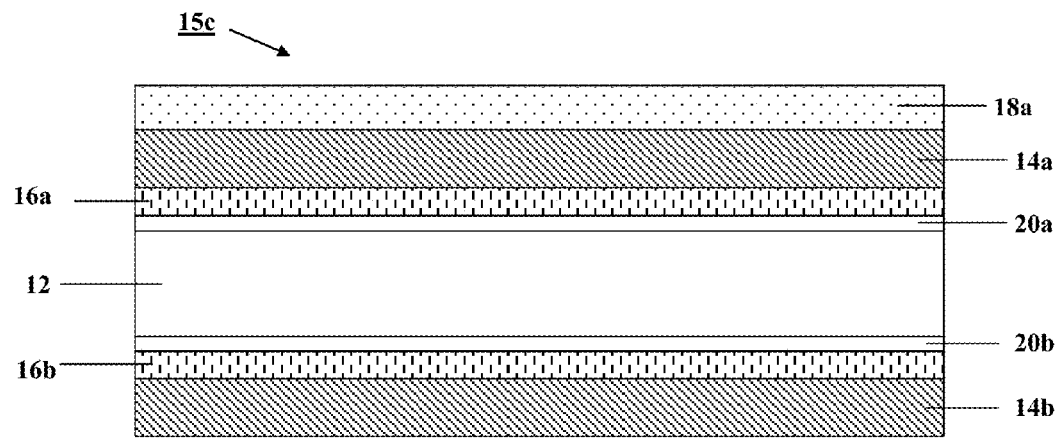

Turning now to FIG. 2C, device 15c includes microcolumn layer 12 with top frit gasket layer 20a disposed on the top surface of microcolumn layer 12, top channel layer 16a disposed on top frit gasket layer 20a, top capping layer 14a disposed on top channel layer 16a, and top port layer 18a disposed on top capping layer 14a. Bottom frit gasket layer 20b is disposed on the bottom surface of microcolumn layer 12, bottom channel layer 16b is disposed on bottom frit gasket layer 20b, and then bottom capping layer 14b is disposed on bottom channel layer 16b.

Figure 2D:
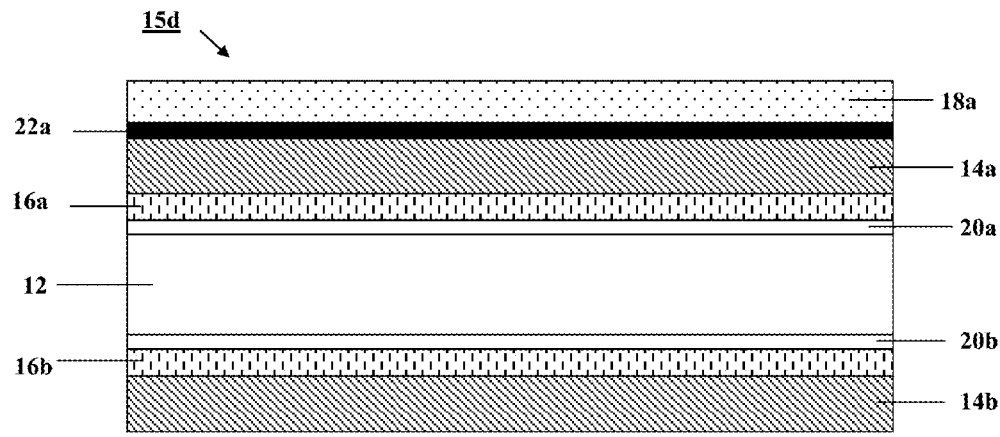

Turning now to FIG. 2D, device 15d includes microcolumn layer 12 with top frit gasket layer 20a disposed on the top surface of microcolumn layer 12, top channel layer 16a disposed on top frit gasket layer 20a, top capping layer 14a disposed on top channel layer 16a, top washer layer 22a disposed on top capping layer 14a, and top port layer 18a disposed on top washer layer 22a. Bottom frit gasket layer 20b is disposed on the bottom surface of microcolumn layer 12, bottom channel layer 16b is disposed on bottom frit gasket layer 20b, and then bottom capping layer 14b is disposed on bottom channel layer 16b.

Figure 2E:
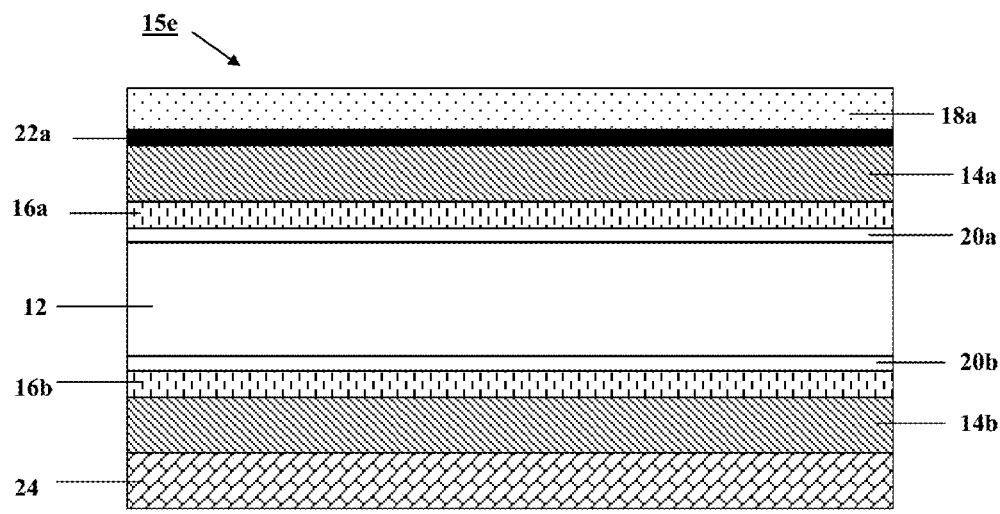

Turning now to FIG. 2E, device 15e includes microcolumn layer 12 with top frit gasket layer 20a disposed on the top surface of microcolumn layer 12, top channel layer 16a disposed on top frit gasket layer 20a, top capping layer 14a disposed on top channel layer 16a, top washer layer 22a disposed on top capping layer 14a, and top port layer 18a disposed on top washer layer 22a. Bottom frit gasket layer 20b is disposed on the bottom surface of microcolumn layer 12, bottom channel layer 16b is disposed on bottom frit gasket layer 20b, bottom capping layer 14b is disposed on bottom channel layer 16b, and then bottom support layer 24 is disposed on bottom capping layer 14b.

Figure 3A:
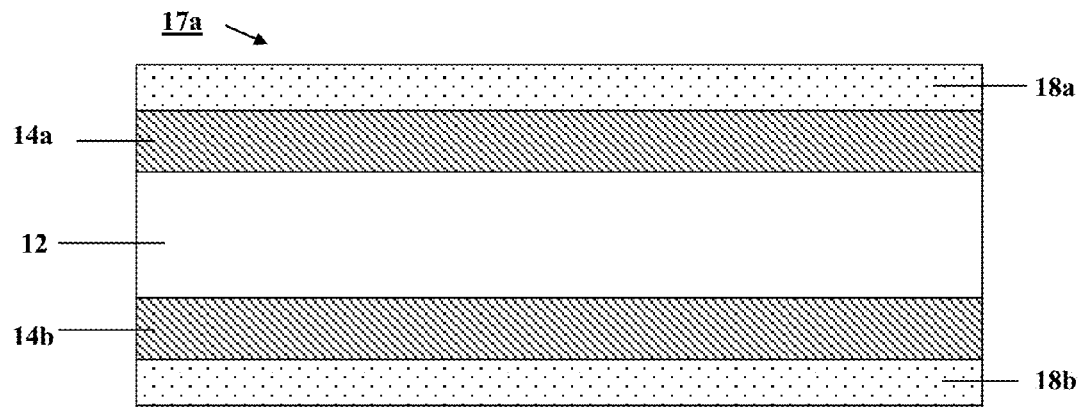
FIGS. 3A-3C are schematics illustrating the layers of embodiments of a microcolumn device of the present disclosure assembled for parallel use.
Figure 3B:
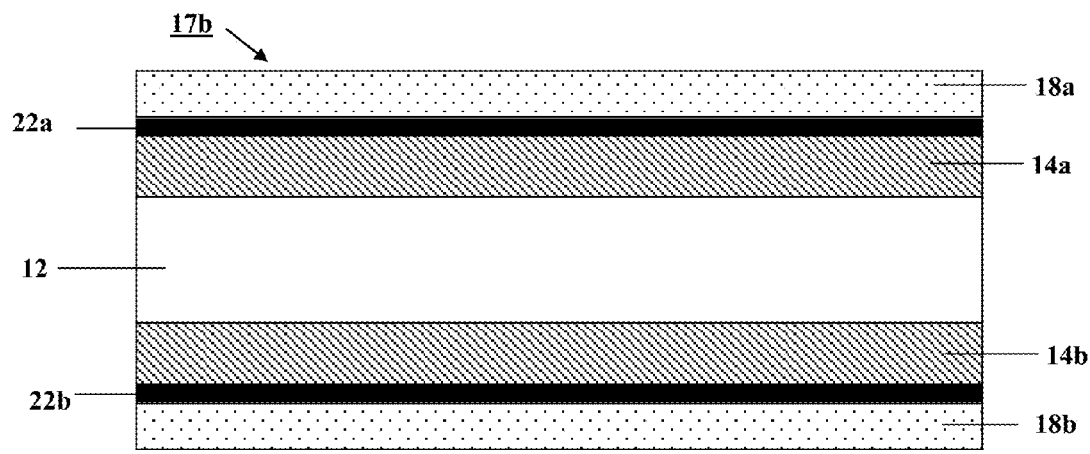
Figure 3C:
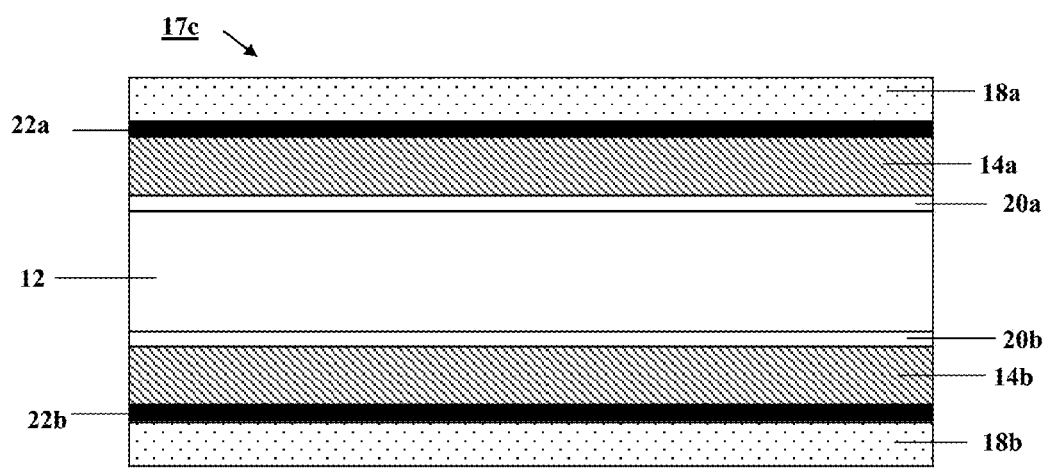

FIGS. 3A-3C are illustrations of various embodiments of the device of the present disclosure in parallel assembly form.

Turning now to FIG. 3A, device 17a includes microcolumn layer 12 with top capping layer 14a disposed on the top surface of microcolumn layer 12, and top port layer 18a disposed on top capping layer 14a. Bottom capping layer 14b is disposed on the bottom surface of microcolumn layer 12, and bottom port layer 18b is disposed on bottom capping layer 14b.

Turning now to FIG. 3B, device 17b includes microcolumn layer 12 with top capping layer 14a disposed on the top surface of microcolumn layer 12, top washer layer 22a disposed on top capping layer 14a, and top port layer 18a disposed on top washer layer 22a. Bottom capping layer 14b is disposed on the bottom surface of microcolumn layer 12, bottom washer layer 22b is disposed on bottom capping layer 14b, and bottom port layer 18b is disposed on bottom washer layer 22b.

Turning now to FIG. 3C, device 17c includes microcolumn layer 12 with top frit gasket layer 20a disposed on the top surface of microcolumn layer 12, top capping layer 14a disposed on top frit gasket layer 20a, top washer layer 22a disposed on top capping layer 14a, and top port layer 18a disposed on top washer layer 22a. Bottom frit gasket layer 20b is disposed on the bottom surface of microcolumn layer 12, bottom capping layer 14b is disposed on bottom frit gasket layer 20b, bottom washer layer 22b is disposed on bottom capping layer 14b, and bottom port layer 18b is disposed on bottom washer layer 22b.

Figure 4A:
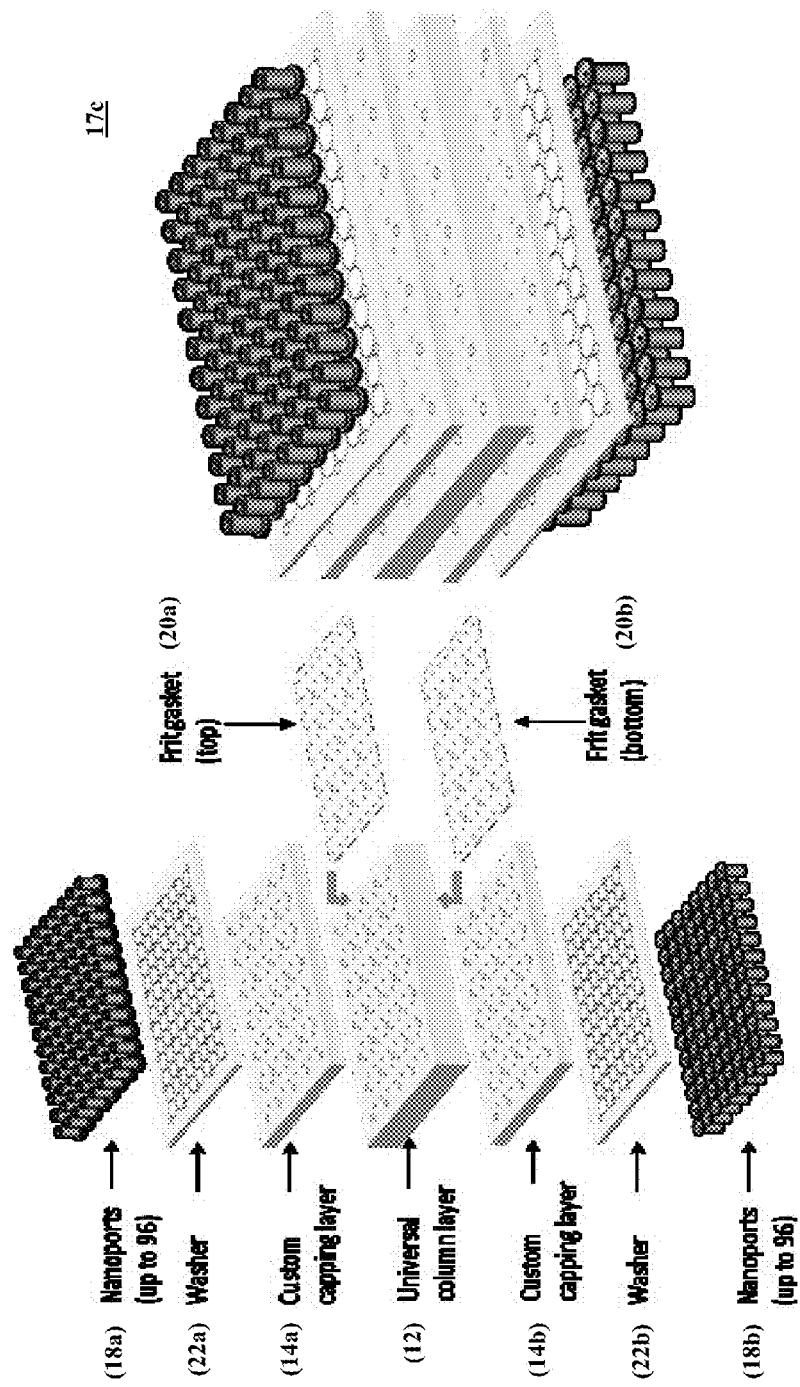
FIGS. 4A-4B are schematics of exploded views of embodiments of a microcolumn device of the present disclosure in parallel assembly (FIG. 4A) and serial assembly (FIG. 4B).
Figure 4B:
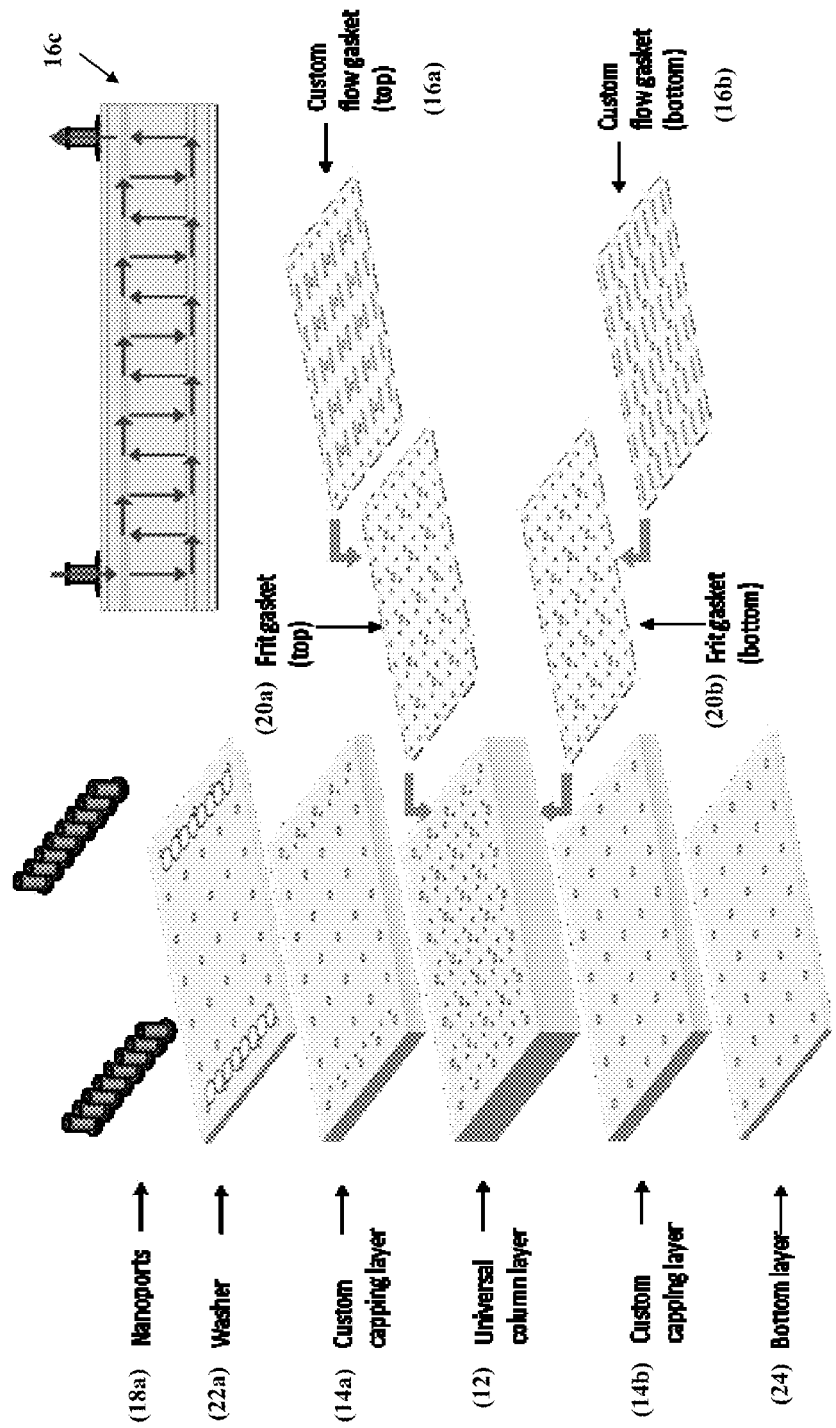

FIGS. 4A-4B are schematics of exploded views of embodiments of a microcolumn device of the present disclosure in parallel assembly (FIG. 4A) and serial assembly (FIG. 4B). The general structure of each of the layers and the components of the layers, if any, is illustrated.

Turning now to FIG. 4A, device 17c (see FIG. 3C) is shown in an exploded view for parallel assembly and function. Device 17c is shown to include microcolumn layer 12 (also denoted as universal column layer) with top frit gasket layer 20a (also denoted as frit gasket (top)) disposed on the top surface of microcolumn layer 12, top capping layer 14a (also denoted as custom capping layer) disposed on top frit gasket layer 20a, top washer layer 22a disposed on top capping layer 14a, and top port layer 18a (also denoted as Nanoports (up to 96)) disposed on top washer layer 22a. Bottom frit gasket layer 20b (also denoted as frit gasket (bottom)) is disposed on the bottom surface of microcolumn layer 12, bottom capping layer 14b (also denoted as custom capping layer) is disposed on bottom frit gasket layer 20b, bottom washer layer 22b is disposed on bottom capping layer 14b, and bottom port layer 18b (also denoted as Nanoports (up to 96)) is disposed on bottom washer layer 22b.

Turning now to FIG. 4b, the device is shown in an exploded view for serial assembly and function. The device is shown to include microcolumn layer 12 (also denoted as universal column layer) with top frit gasket layer 20a (also denoted as frit gasket (top)) disposed on the top surface of microcolumn layer 12, top channel layer 16a (also denoted as custom flow gasket (top)) disposed on top frit gasket layer 20a, top capping layer 14a (also denoted as custom capping layer) disposed on top channel layer 16a, top washer layer 22a disposed on top capping layer 14a, and top port layer 18a (also denoted as Nanoports) disposed on top washer layer 22a. Bottom frit gasket layer 20b (also denoted as frit gasket (bottom)) is disposed on the bottom surface of microcolumn layer 12, bottom channel layer 16b (also denoted as custom flow gasket (bottom)) is disposed on bottom frit gasket layer 20b, bottom capping layer 14b is disposed on bottom channel layer 16b, and bottom support layer 24 (also denoted as bottom layer) is disposed on bottom capping layer 14b.

The present disclosure also provides methods of making the devices described herein. In view of the teachings set forth in the present disclosure, including, without limitation, the examples and the drawings discussed herein, one of ordinary skill can readily understand how to make the devices of the present disclosure.

In another aspect, the present disclosure provides a system for collecting one or more liquid sample from an affinity chromatography microcolumn device of the present disclosure. In one embodiment, the system comprises: (i) a device for conducting affinity chromatography in multiple microcolumns in parallel and/or in series, the device being a device as provided herein; (ii) a liquid flow mechanism for moving a liquid sample into, through, and out of a microcolumn contained in the devices; and (iii) a liquid collection apparatus comprising well portions for collecting liquid samples from the microcolumns, where each well portion is aligned with a single corresponding microcolumn for collection of the liquid sample therefrom. In an alternative embodiment, the liquid collection apparatus can comprise other structures that can function to collect liquid samples from each microcolumn in an organized manner, without the liquid collection apparatus including well portions. For example, instead, the well portions can be replaced with a tube or other sort of conduit that is in fluid alignment with a particular microcolumn so as to collect the liquid sample from that particular microcolumn.

The liquid flow mechanism can be any apparatus or technology suitable for causing the liquid samples to enter the desired microcolumns in a manner sufficient to conduct the affinity chromatography in the microcolumns. The liquid flow mechanism can be also be any apparatus or technology suitable for causing the liquid samples to enter the desired microcolumns in a manner sufficient to conduct the affinity chromatography in the microcolumns, as well as to for causing the liquid sample to exit the microcolumns. By exiting the microcolumns, the liquid samples that have undergone affinity chromatography in the microcolumns can then be collected for further analyses in accordance with the present disclosure. In a particular embodiment, the liquid flow mechanism is programmable to move the liquid samples through the microcolumns at a desired flow rate, at a desired volume, for a desired amount of time, and/or for a desired time interval.

Suitable liquid flow mechanisms in accordance with the present disclosure can include, without limitation, a pump for either pushing or pulling the liquid sample through one or more of the microcolumns. In a particular embodiment, the pump controls flow rate of the liquid samples through the microcolumns.

In accordance with the system described herein, the liquid collection apparatus can be any apparatus suitable for collecting the liquid samples once they exit the microcolumns. In a particular embodiment the liquid collection apparatus can include, without limitation, a microplate having a plurality of wells for collecting liquid samples from the microcolumns. Suitable microplates can include any plate that includes one or more well that can capture and hold liquid samples that exit from the microcolumns of the device of the present disclosure. In particular embodiments, the microplate is a standard microwell plate that includes the standard number and size of wells. Examples of the number of wells in a suitable microplate can include, without limitation, 6, 12, 24, 48, 96, 384, 1536, 3456, and 9600 wells.

Figure 5:
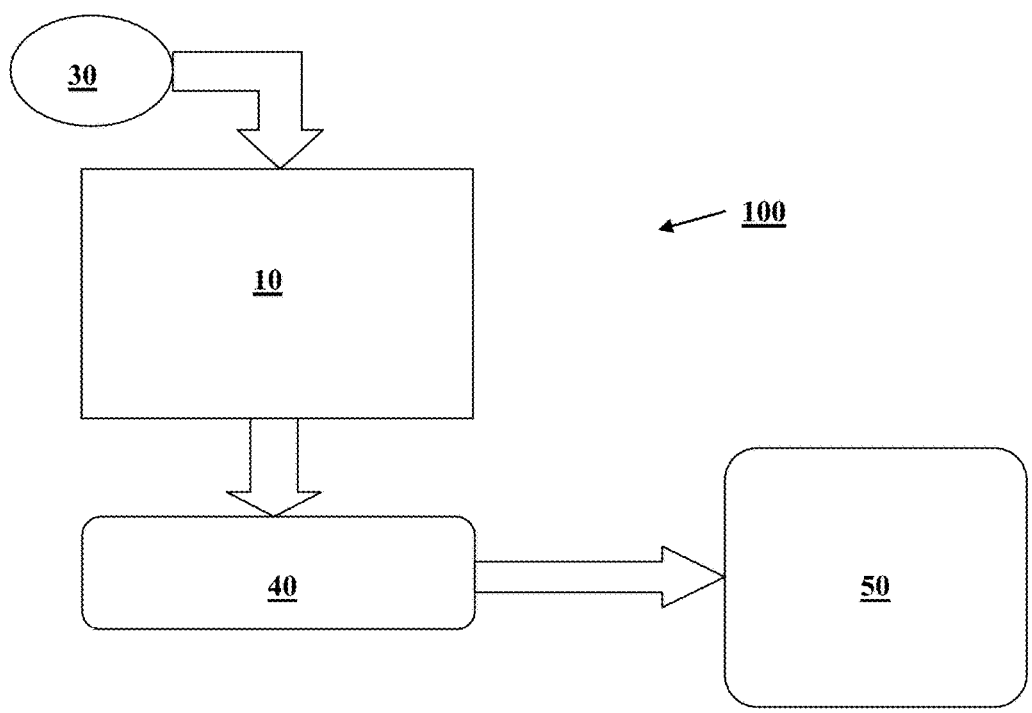
FIG. 5 is a schematic illustrating one embodiment of a system of the present disclosure.

FIG. 5 is a schematic illustrating one embodiment of a system of the present disclosure. As shown in FIG. 5, system 100 includes liquid flow mechanism 30 which provides liquid samples to microcolumn device 10 for affinity chromatography. Microcolumn device 10 is in fluidic communication with liquid collection apparatus 40, which collects the liquid samples that run through the microcolumns of microcolumn device 10. Liquid collection apparatus 40 then provides the collected liquid samples that have undergone affinity chromatography to downstream analytic apparatus or system 50.

The present disclosure also provides methods of making the systems described herein. In view of the teachings set forth in the present disclosure, including, without limitation, the examples and the drawings discussed herein, one of ordinary skill can readily understand how to make the systems of the present disclosure.

In yet another aspect, the present disclosure provides a method of collecting one or more liquid sample from an affinity chromatography microcolumn for further analysis. In one embodiment, this method comprises: (i) providing a system for collecting one or more liquid sample from an affinity chromatography microcolumn device, the system being a system as described and contemplated herein; (ii) running one or more liquid sample through the microcolumns of the device of the system, either in a parallel manner or a serial manner or in both a parallel and serial manner, under conditions effective to allow a test agent contained in the liquid sample to bind specifically to a target molecule contained in the microcolumn of the device; and (iii) recovering from each microcolumn the test agent or test agents that bind specifically to the respective target molecules of each microcolumn device, the recovering taking place in the liquid collection apparatus.

In one embodiment of this method, the recovering step comprises the steps of: washing unbound and weakly bound test agents from each microcolumn; and eluting the test agents that specifically bind to the target molecules of each microcolumn.

In accordance with one embodiment of this method, the recovered test agents that specifically bind to the target molecules are nucleic acid aptamers comprising RNA aptamers. In such an embodiment, the method can further comprise performing reverse transcription amplification of the selected aptamer population.

In accordance with one embodiment of this method, the method can further comprise purifying and sequencing the amplified aptamer population.

In accordance with another embodiment of this method, the recovering, performing reverse transcription amplification, purifying, and/or sequencing steps are performed in one or more separate fluidic devices coupled in fluidic communication with the microcolumn devices of the present disclosure. Such separate fluidic devices are known in the relevant art by those of ordinary skill in the art.

In accordance with one embodiment of this method, each of the running and recovering steps is automated.

In accordance with another embodiment of this method, the liquid samples collected from the microcolumns are further used in analytical processes. Any analytical process suitable for use with microcolumn affinity chromatography is contemplated by the present disclosure. In certain embodiments, the analytical processes can involve, without limitation, high throughput processes, quantitative polymerase chain reaction (qPCR), UV-Visual absorption spectroscopy, fluorescence spectroscopy, nucleic acid sequencing (e.g, DNA sequencing), and mass spectrometry.

Provided below are descriptions of further embodiments, aspects, and uses of the microcolumn device and system of the present disclosure.

Features of Various Embodiments of a Device of the Present Disclosure

In various embodiments, the device of the present invention is unique in that it is the first application of affinity chromatography using the standards resins to a microplate-based format, especially for aptamer selections. Existing formats require binding or adsorption to the surface of a microplate. The device of the present disclosure allows for the exploitation of non-equilibrium flow parameters to optimize the SELEX process, and also to perform these selections to a tremendous number of targets (e.g., up to 96). This also allows for high throughput characterization and optimization of the binding parameters which has already generated valuable data regarding both specific aptamer binding phenomena, as well as background binding issues.

In various embodiments, the device of the present disclosure can be configured to run in parallel or serial configurations, or both. This is achieved through silicone gaskets that contain the program/information on column connectivity that can be quickly and cheaply made in minutes with the $CO_2$ laser. Because of the speed and ease of fabrication, programmed Capping Layers can be fabricated, however, in certain embodiments, this is not entirely necessary, as one could incorporate a 3rd gasket to prevent flow out of undesired input/output ports from the standard parallel mode Caps.

In various embodiments, because of the requirements of Serial mode selections, the device has been engineered to operate with flow in both the forward and reverse directions. This enables the device to be use with a pump in either push or pull modes depending on weather buffers need to be delivered from a syringe, or drawn up from a reservoir, or similarly if samples need to be collected INTO a syringe by drawing up solution.

The Serial mode allows for more complex and sophisticated selections to be performed, to either do one or several sequential negative selections, or partition the starting library among many (dissimilar) targets, or to partition enriched pools that bind to a large protein or complex, into sub-pools that bind to distinct subunits or domains of the target. If many serial selections are required, especially simple negative selections, then two (or more) middle Layers can be connected together, providing 192 (or more) columns that could be used for 96 serial selections, each with a negative selection preceding a target selection. In various embodiments, this mode would entail removing the "Negative column Layer" before washing and eluting bound samples.

Finally, in various embodiments, the design of the device of the present disclosure allows it to complement microplate-based processes and technologies. This not only allows for simpler and higher throughput processing of samples, but also allows for potential automation through Liquid Handling workstations that are designed for standard plate layouts.

Various Embodiments

Various embodiments of the device of the present disclosure are further described herein below.

Microplate-Based Enrichment Device Used for the Selection of Aptamers (MEDUSA)

One example of an embodiment of a device of the present invention is described below. As used herein, in one embodiment, the device can be referred to as a Microplate-based Enrichment Device Used for the Selection of Aptamers (MEDUSA). Provided below is a description of the fabrication of various embodiments of the device, a description of suitable components of various embodiments of the device, and the operation of various embodiments of the device.

Fabrication of a 96× Selection Device

The device can be fabricated through conventional machining similar to previously reported microcolumns. However, with respect to large format devices, laser machining via $CO_2$ at 10.6 μm allows for complete reproducibility by designing and executing a CAD file, and simply "printing" the outline in sheets of PMMA thermoplastic (Plexiglas). It also allows for the fabrication of an entire device much faster and much more cheaply than before. In various embodiments of the present disclosure, a complete device (7-9 Layers) can be machined in about 1 hour.

Device Components

In various embodiments, the device of the present disclosure can include, without limitation, one or more of the following components: a universal column layer; universal frit gaskets; custom capping layers; custom flow gaskets; and washers. Exemplary embodiments of these components are described below.

Figure 6:
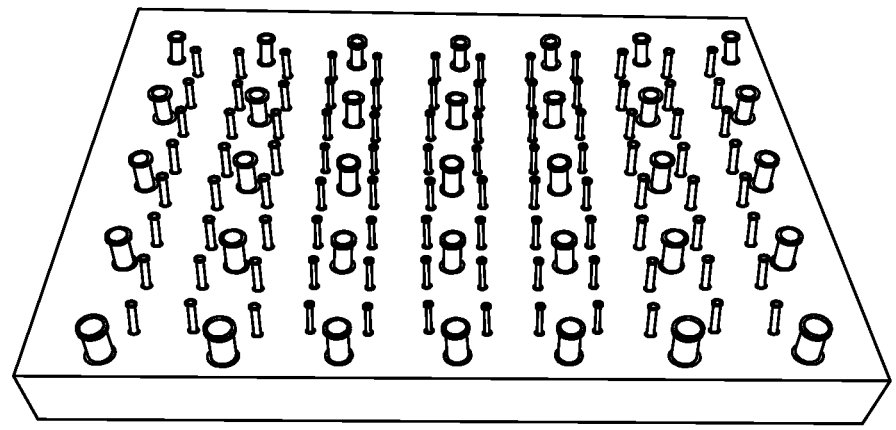
FIG. 6 is a photograph of one embodiment of a microcolumn layer of a device of the present disclosure.

One component of a device of the present disclosure is a universal column layer. In one embodiment, the universal column layer can comprise PMMA (e.g., ½" PMMA). In various embodiments, the universal column layer can contain 96 microcolumns spaced 9×9 mm according to standard 96-well microplate specifications, although the number of microcolumns and spacing can be more or less than as described. In various embodiments, the universal column layer can further contain 35 threaded holes (5-40) for bolting the various device layers together. FIG. 6 illustrates one embodiment of a universal column layer of the present disclosure.

Figure 7:
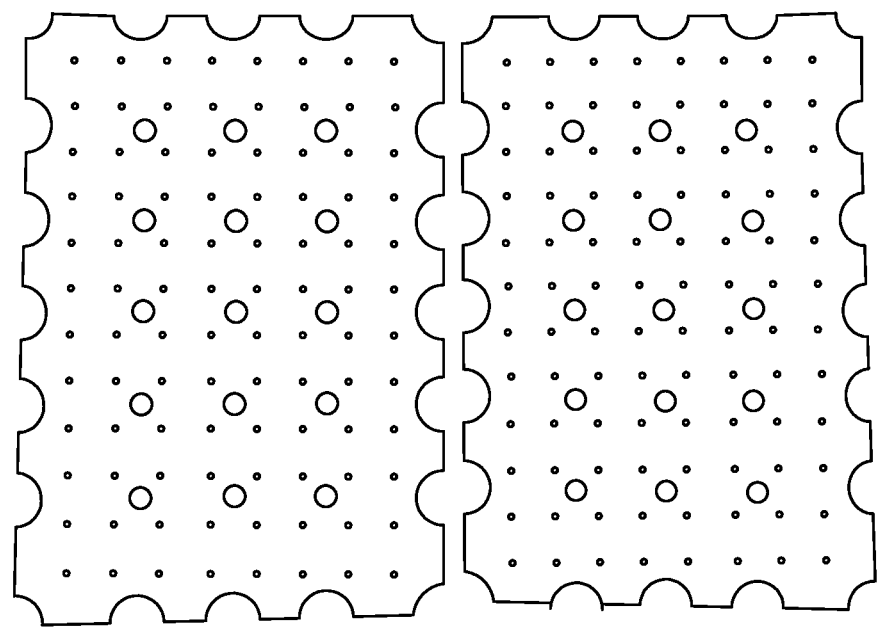
FIG. 7 is a photograph of embodiments of universal frit gaskets (top or bottom frit gaskets) of a device of the present disclosure.
Figure 8:
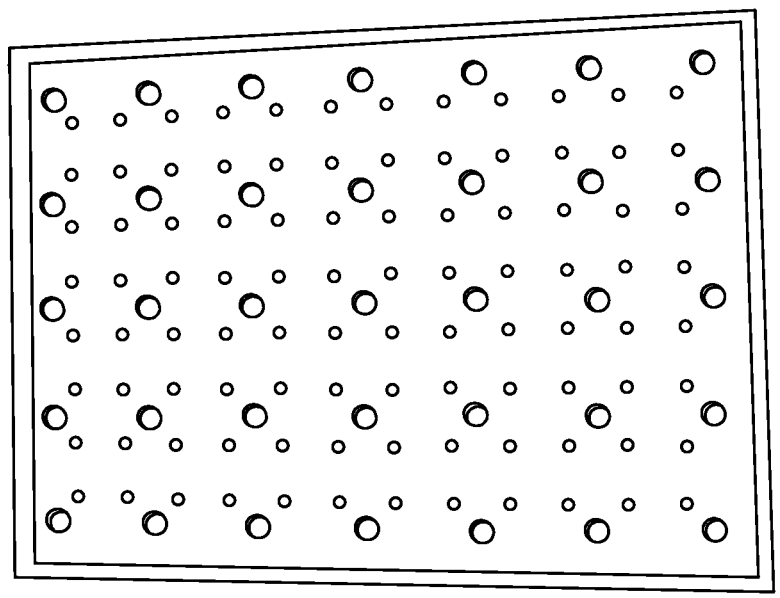
FIG. 8 is a photograph of one embodiment of a frit gasket of a device of the present disclosure.
Figure 9:
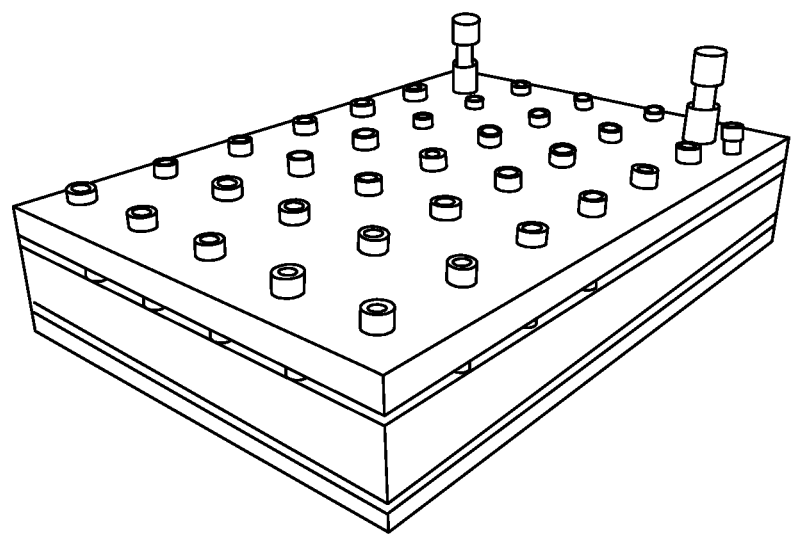
FIG. 9 is a photograph of one embodiment of a capping layer of a device of the present disclosure.
Figure 10:
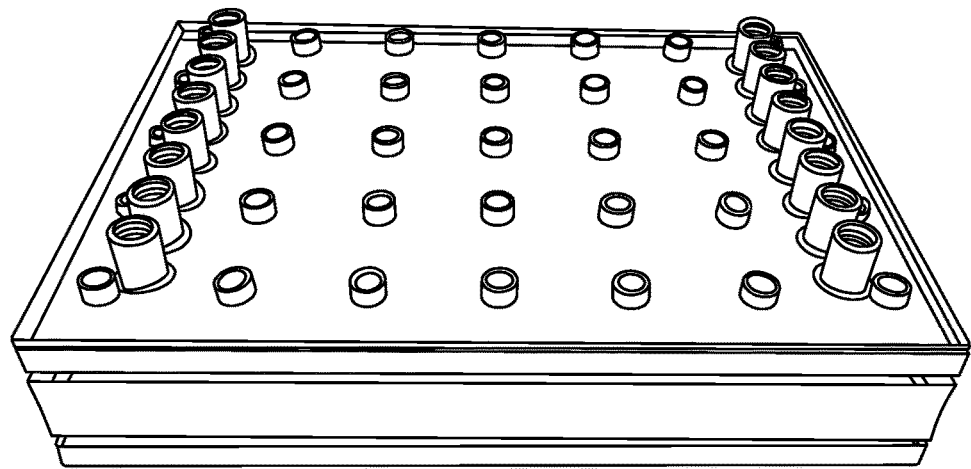
FIG. 10 is a photograph of one embodiment of a capping layer of a device of the present disclosure.
Figure 11:
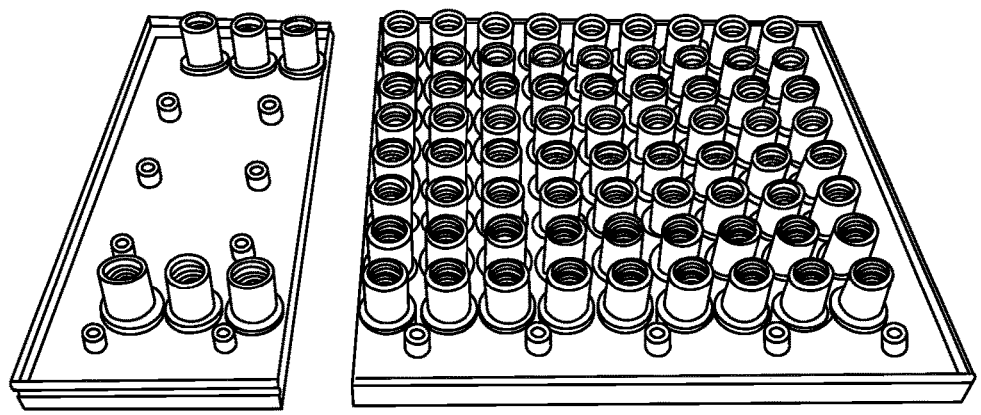
FIG. 11 is a photograph of one embodiment of a capping layer of a device of the present disclosure.
Figure 12:
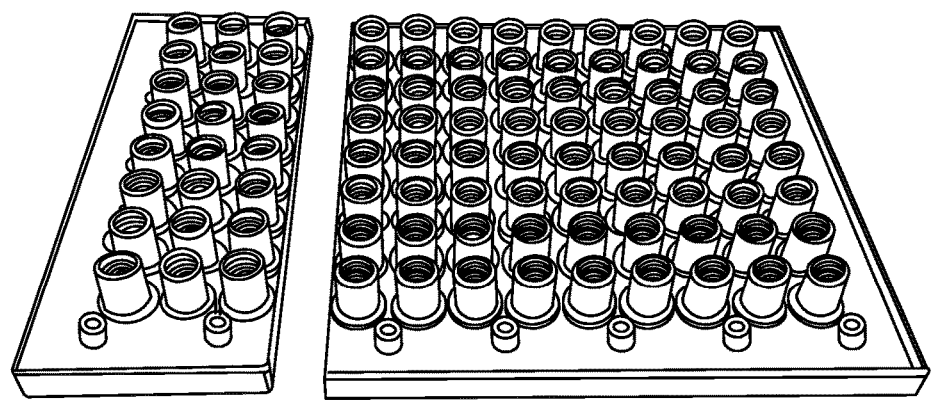
FIG. 12 is a photograph of one embodiment of a capping layer of a device of the present disclosure.

Another component of a device of the present disclosure is a universal frit gasket or universal frit gaskets. In one embodiment, the universal frit gaskets can comprise silicone (e.g., 1/16") with adhesive back. In various embodiments, the universal frit gaskets can contain, without limitation, 96 2 mm diameter holes for 2 mm diameter polyethylene (or other material) frits and 35 through holes for 5-40 screws. The universal frit gaskets can be used on both the TOP and BOTTOM of the middle layer for flow in BOTH directions. FIG. 7 and FIG. 8 illustrate various embodiments of the universal frit gaskets of the present disclosure.

Another component of a device of the present disclosure is a custom capping layer or custom capping layers. In one embodiment, the custom capping layers can comprise PMMA (e.g., ¼" PMMA). In various embodiments, the custom capping layers can be, without limitation, top and bottom are custom designed according to desired flow path (e.g., 96 in Serial or 96 in Parallel or something in between). The caps can contain the program/information on column connectivity. Further, the caps can contain desired numbers (e.g., up to 96) of Input/Output holes for the device, each input/output containing a bonded NanoPort, for example. The caps can also contain through holes for 5-40 screws. FIG. 9, FIG. 10, FIG. 11, and FIG. 12 illustrate embodiments of custom capping layers of the present disclosure.

Figure 13:
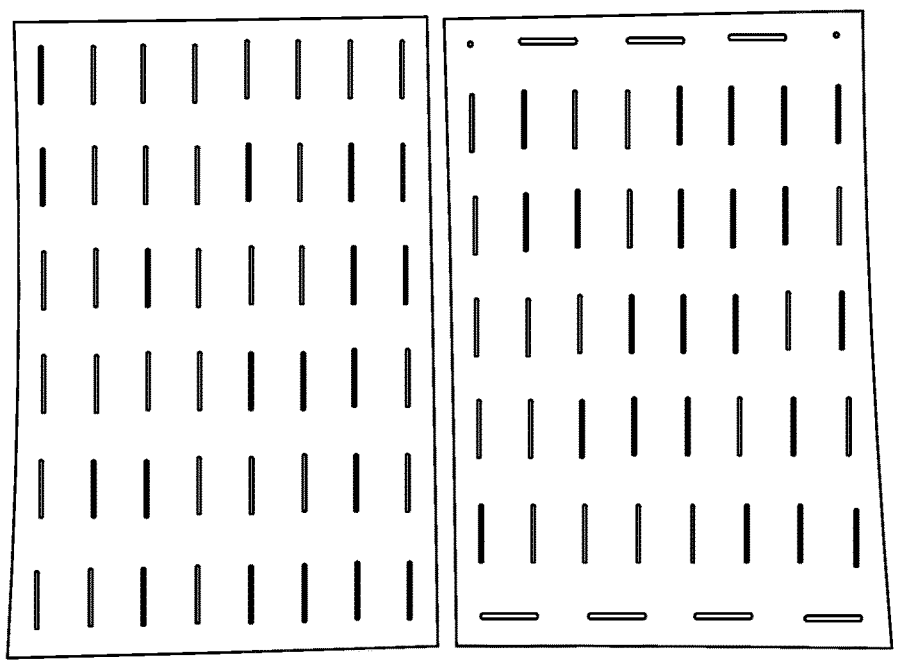
FIG. 13 is a photograph of embodiments of custom flow gaskets (also referred to herein as top channel layers or bottom capping layers when in series) of a device of the present disclosure.
Figure 14:
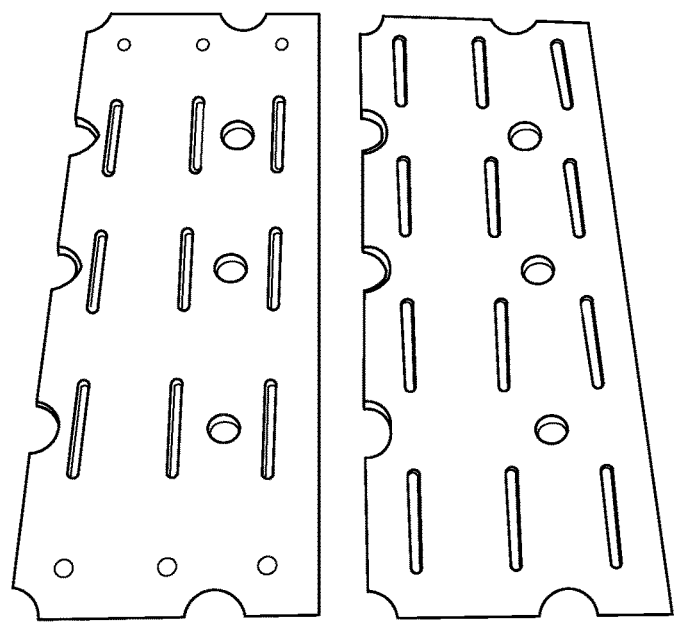
FIG. 14 is a photograph of embodiments of custom flow gaskets (also referred to herein as top channel layers or bottom capping layers when in series) of a device of the present disclosure.

Another component of a device of the present disclosure is a custom flow gasket or custom flow gaskets. In one embodiment, the custom flow gaskets can comprise silicone (1/32" silicone)—no adhesive. In various embodiments, the custom flow gaskets can contain, without limitation, the following: (i) input and output holes that contain the program/information on column connectivity; (ii) flow channels that contain the program/information on column connectivity and sample-to-sample communications; and (iii) through holes for 5-40 screws. In various embodiments, this layer is not needed for devices operated in parallel configurations. FIG. 13 and FIG. 14 illustrate various embodiments of custom flow gaskets of the present disclosure.

Figure 15:
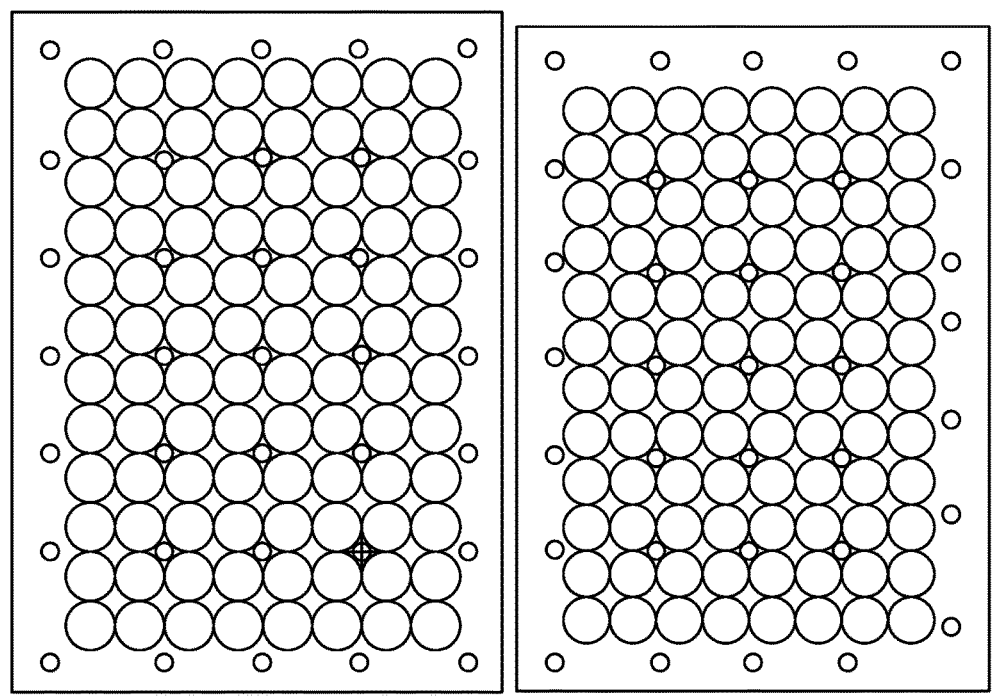
FIG. 15 is a photograph of embodiments of washer layers of a device of the present disclosure.
Figure 16:
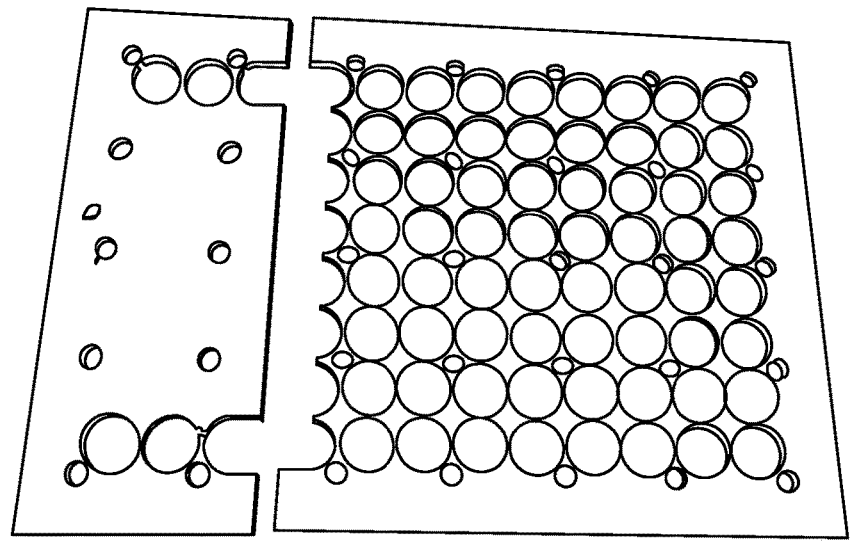
FIG. 16 is a photograph of embodiments of washer layers of a device of the present disclosure.
Figure 17:
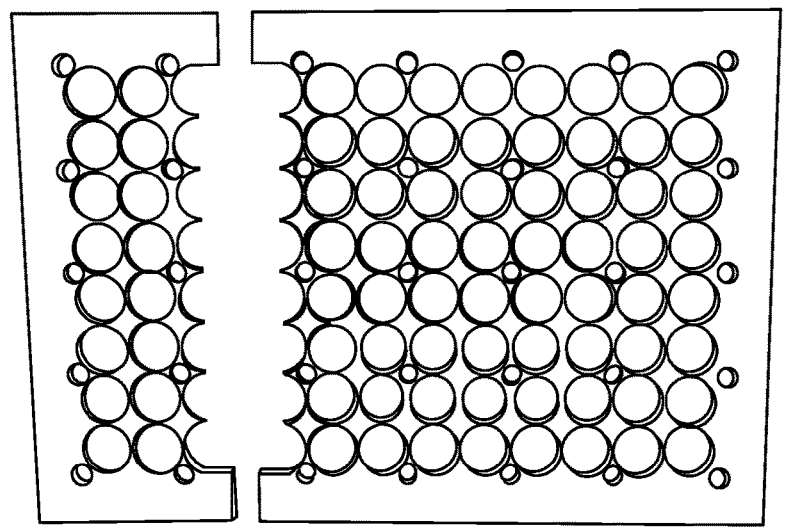
FIG. 17 is a photograph of embodiments of washer layers of a device of the present disclosure.

Another component of a device of the present disclosure is a washer. In one embodiment, the washer comprises PMMA (e.g., 1 mm PMMA). In various embodiments, the washers provide a load bearing layer for bolting all the layers together (e.g., prevents screw heads from putting loads on the foot of the Nanoports), contains large holes to sit around all input/output Nanoports, and contains through holes for 5-40 screws. FIG. 15, FIG. 16, and FIG. 17 illustrate embodiments of washers of the present disclosure.

Figure 18:
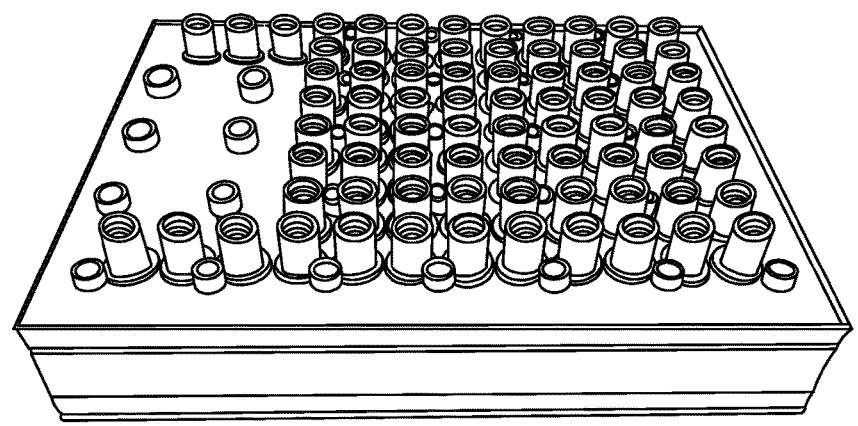
FIG. 18 is a photograph of one embodiment of a microcolumn device of the present disclosure.
Figure 19:
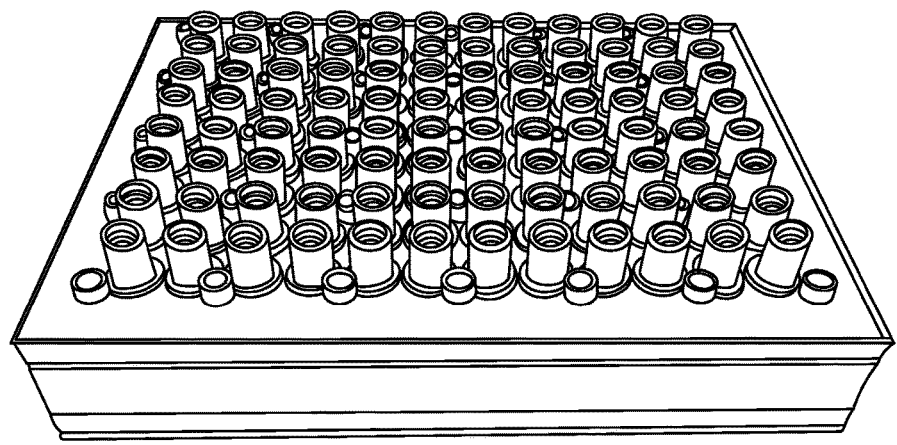
FIG. 19 is a photograph of one embodiment of a microcolumn device of the present disclosure.

Illustrative examples of embodiments of fully assembled devices of the present disclosure are shown in FIG. 4 (parallel assembly), FIG. 5 (serial assembly), FIG. 18, and FIG. 19. In various embodiments, the fully assembled device can be configured so that all Layers are aligned and bolted together to create a liquid tight seal.

In various embodiments, in the case of the ALL SERIAL configuration, the bottom layers are simply the cap in ¼" plastic that contains through holes for bolting, and the bottom most layer in 1 mm thick plastic. In certain embodiments of the ALL SERIAL configuration, the "washer" and load bearing layer with through holes for the screws are not necessary. However, it can be included to keep the device in the same total thickness; especially when there are both serial and parallel configurations going on at the same time—it keeps the screw depth and device thickness equal throughout.

Operation of the Device

Provided below is a description of one embodiment of the operation of particular embodiments and aspects of the device of the present disclosure. FIG. 20 provides a schematic of one exemplary experiment utilizing both serial and parallel selections simultaneously. As shown in this figure, "(II)" indicates Parallel modes and "[ ]" indicates concentration.

As shown in FIG. 8, the middle layer, which has the silicone frit gaskets adhered to both sides, has Frits inserted into all 96 microcolumns on ONE side. This is to retain injected Resin from the bottom side.

Figure 21:
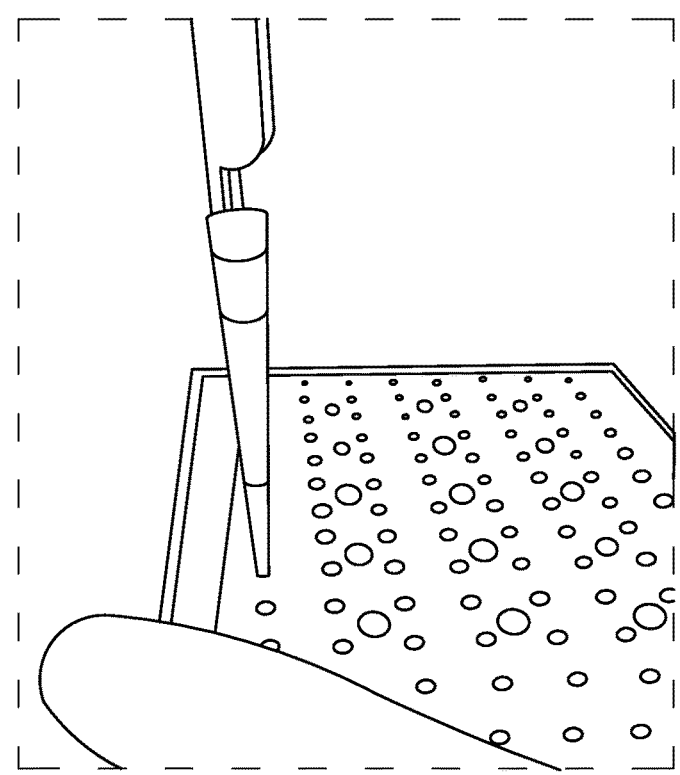
FIG. 21 is a photograph illustrating injecting of protein functionalized resin (e.g., GFP) into a microcolumn of one embodiment of a device of the present disclosure.

As shown in FIG. 21, the device is then turned over, and protein functionalized resins (such as GFP as shown) are injected into each column, and then a Frit is added to retain the resin from the top.

Figure 22:
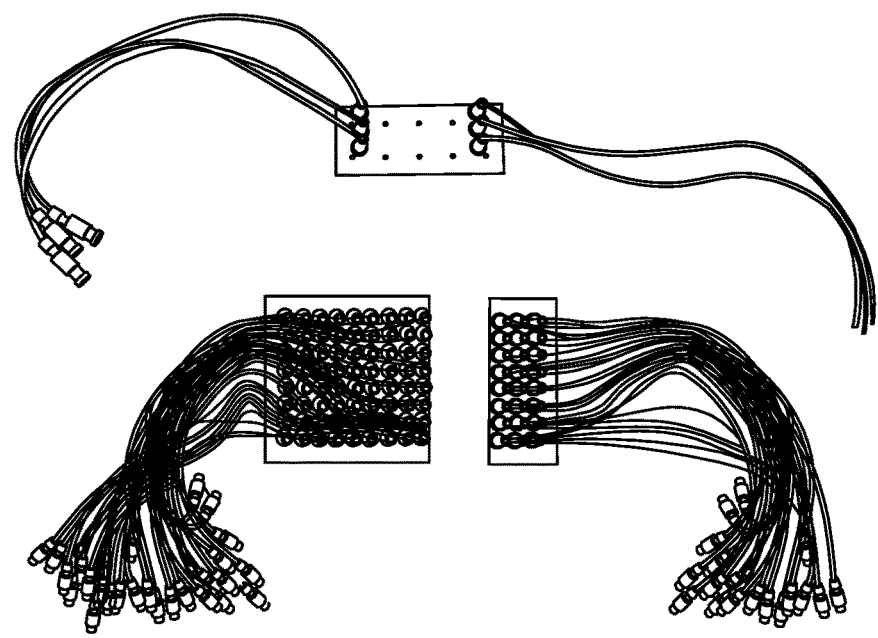
FIG. 22 is a photograph of various embodiments of caps of a microcolumn device of the present disclosure having connectors, tubing, and other fluidic components attached.
Figure 23:
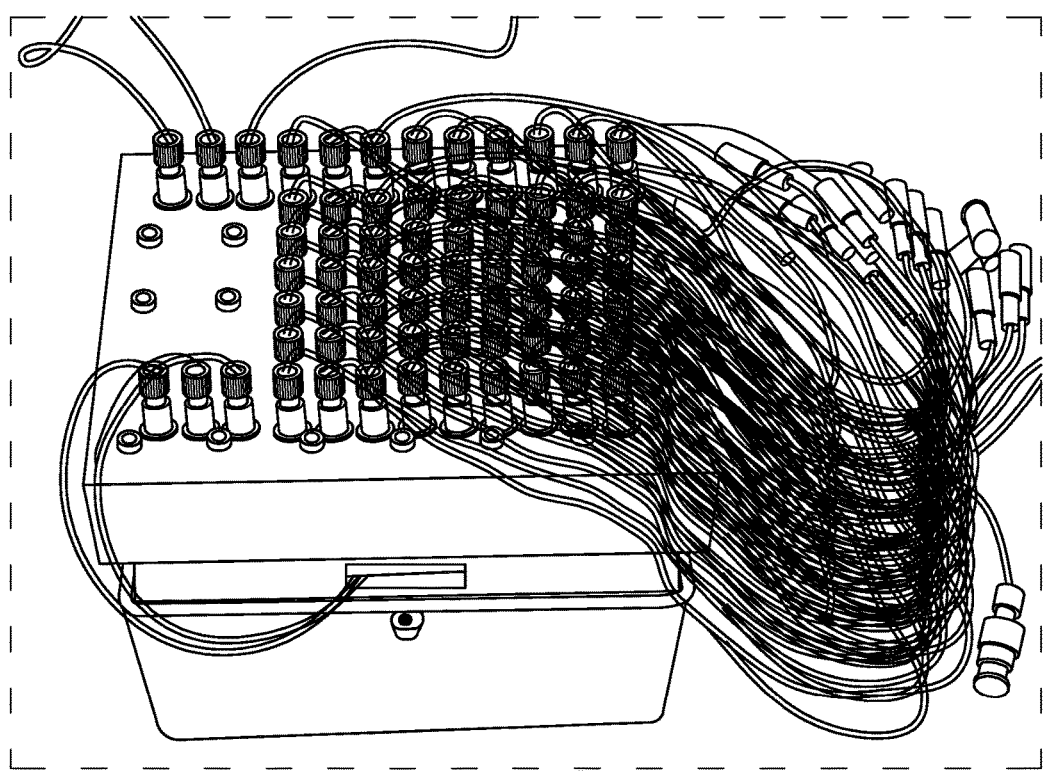
FIG. 23 is a photograph of an embodiment of caps of a microcolumn device of the present disclosure having connectors, tubing, and other fluidic components attached.

As shown in FIG. 22 and FIG. 23, the caps are then bolted to the Top and Bottom. As shown, the caps already have the connectors, tubing and other fluidic components attached.

The above illustrated experiment includes 72 selections being performed in Parallel, and 3 selections being performed with 8 targets each in series. The RNA libraries for each are injected and the waste flows out into the purple waste reservoir which is a 1 mL pipette Tip box which has the same 9×9 mm microplate spacing, and whose holes are large enough to accommodate the width of the Nanoports.

Figure 24:
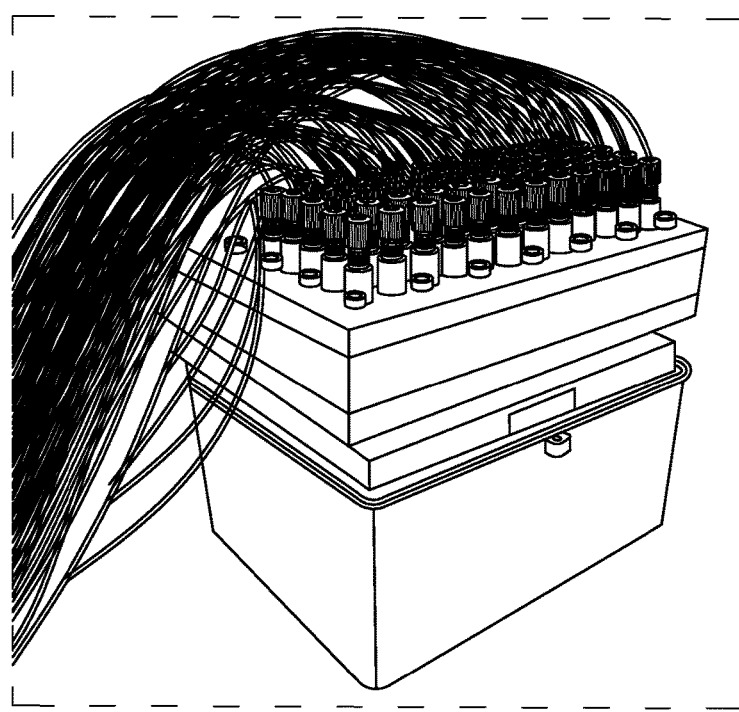
FIG. 24 is a photograph of an embodiment of a microcolumn device of the present disclosure having connectors, tubing, and other fluidic components attached.

As shown in FIG. 24, the serial devices can then be reconfigured to run in parallel for the Washes to prevent rebinding and contamination of RNA in downstream columns.

Figure 25:
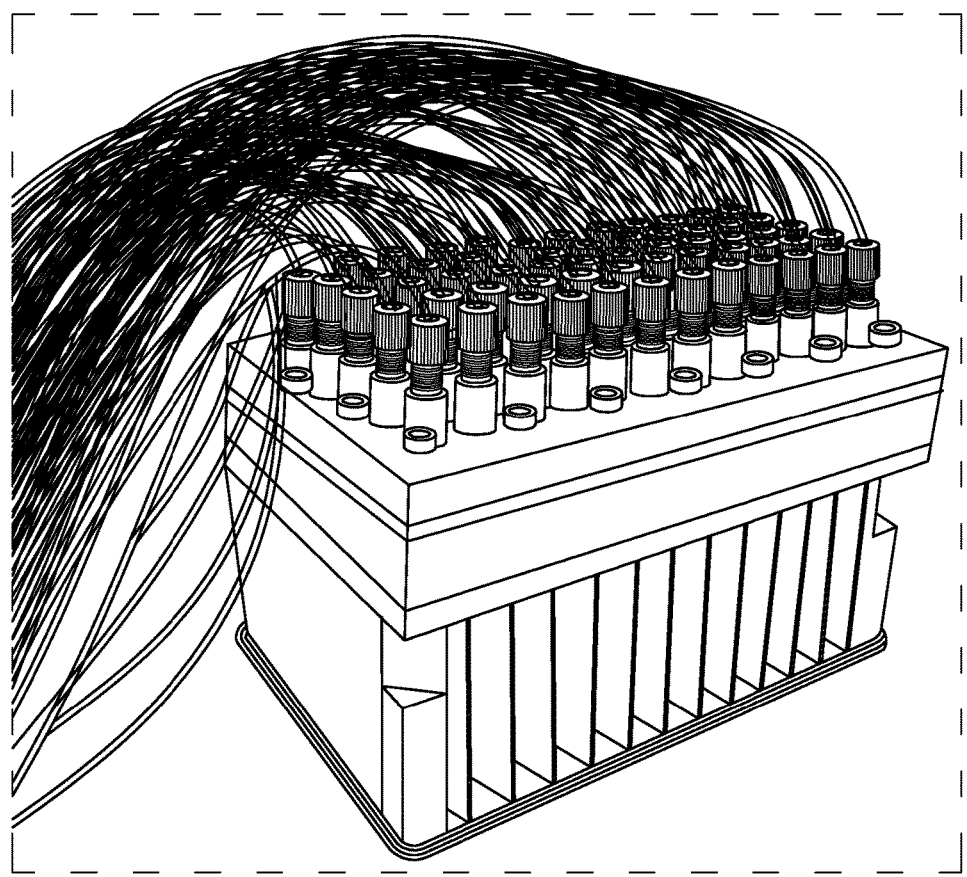
FIG. 25 is a photograph of an embodiment of a microcolumn device of the present disclosure having connectors, tubing, and other fluidic components attached.

As shown in FIG. 25, elutions are performed next by placing the device into a large volume (2 mL) microplate for sample collection.

Figure 26:
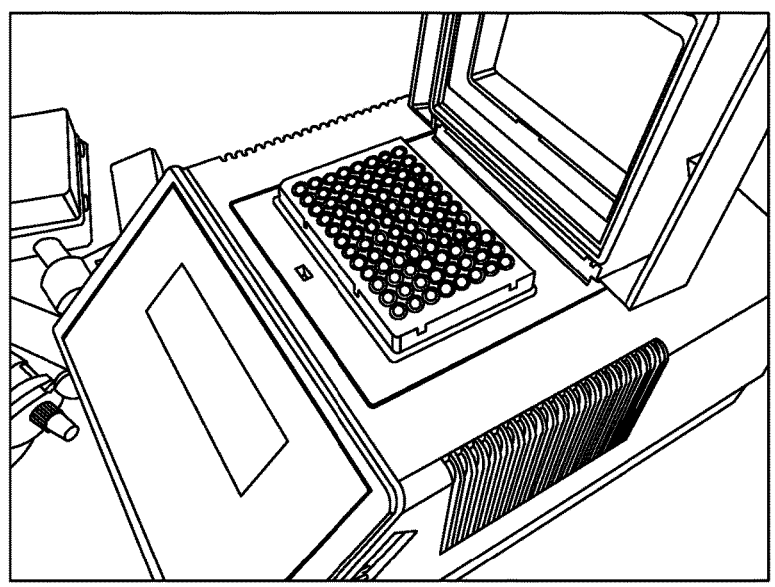
FIG. 26 is a photograph of a liquid collection apparatus and downstream analytic apparatus for use with a microcolumn device of the present disclosure.
Figure 27:
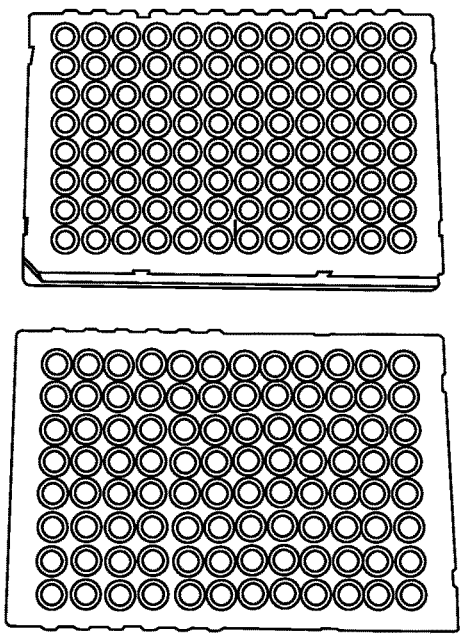
FIG. 27 is a photograph of liquid collection apparatuses for use in downstream analytics with a microcolumn device of the present disclosure.

As shown in FIG. 26 and FIG. 27, downstream processes such as Reverse Transcription can be continued in a plate based format. In certain embodiments, 2 plates are used.

Figure 28:
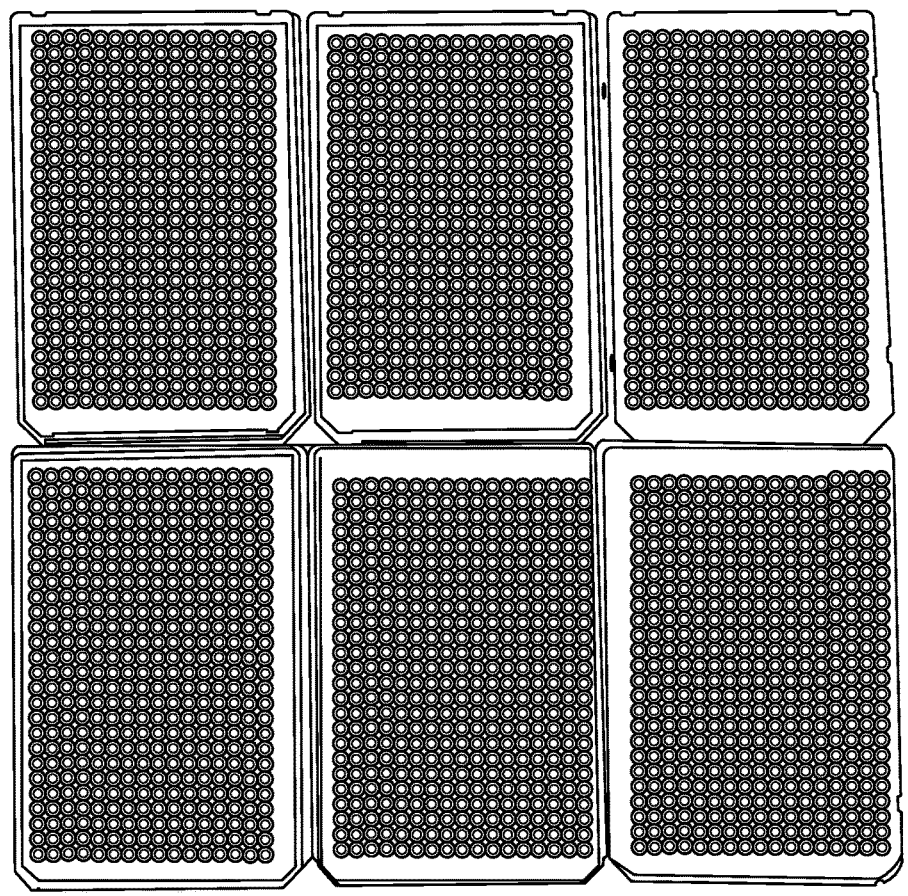
FIG. 28 is a photograph of various liquid collection apparatuses for use with a microcolumn device of the present disclosure.

As shown in FIG. 28, quantification of the samples is also performed in a plate based format. This time using 384 Well plates for qPCR. In certain embodiments, 6 plates were used to fully quantify all of the samples.

Using various embodiments of the device of the present disclosure, experiments we effective to generate a tremendous amount of data, testing 6 different RNA species, to 8 different targets; as well as testing an hypothesis about steric hindrance and optimal binding concentrations to 3 targets at 8 different concentrations. ALL experiments were performed in Triplicate to generate the necessary statistics for every parameter; all in a SINGLE device and experiment. Results are shown in the graphs provided in FIG. 39 and FIG. 40.

Additional Embodiments

Figure 29:
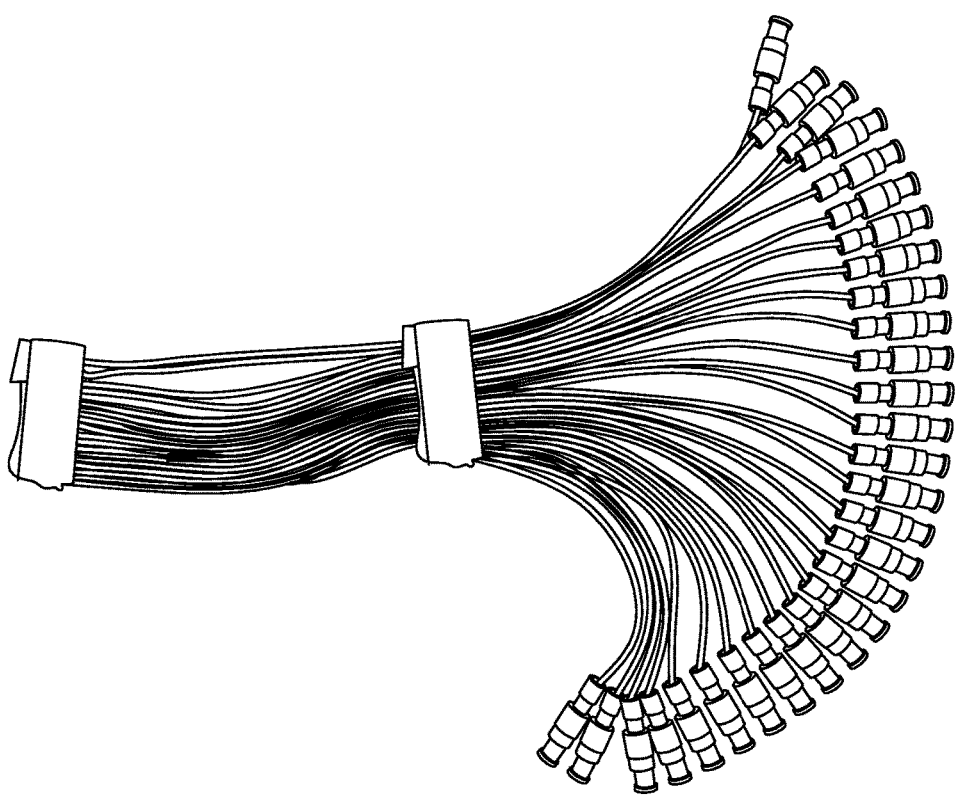
FIG. 29 is a photograph of a fluidic "ribbon" for use with a microcolumn device of the present disclosure.
Figure 30:
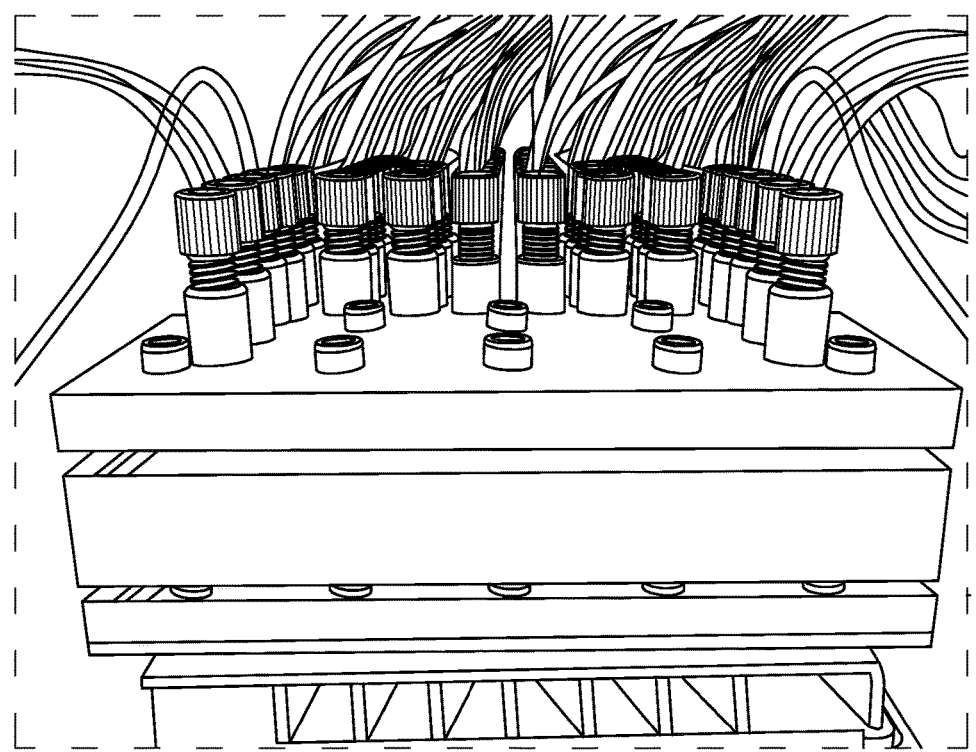
FIG. 30 is a photograph of aspects of microcolumn device of the present disclosure.
Figure 31:
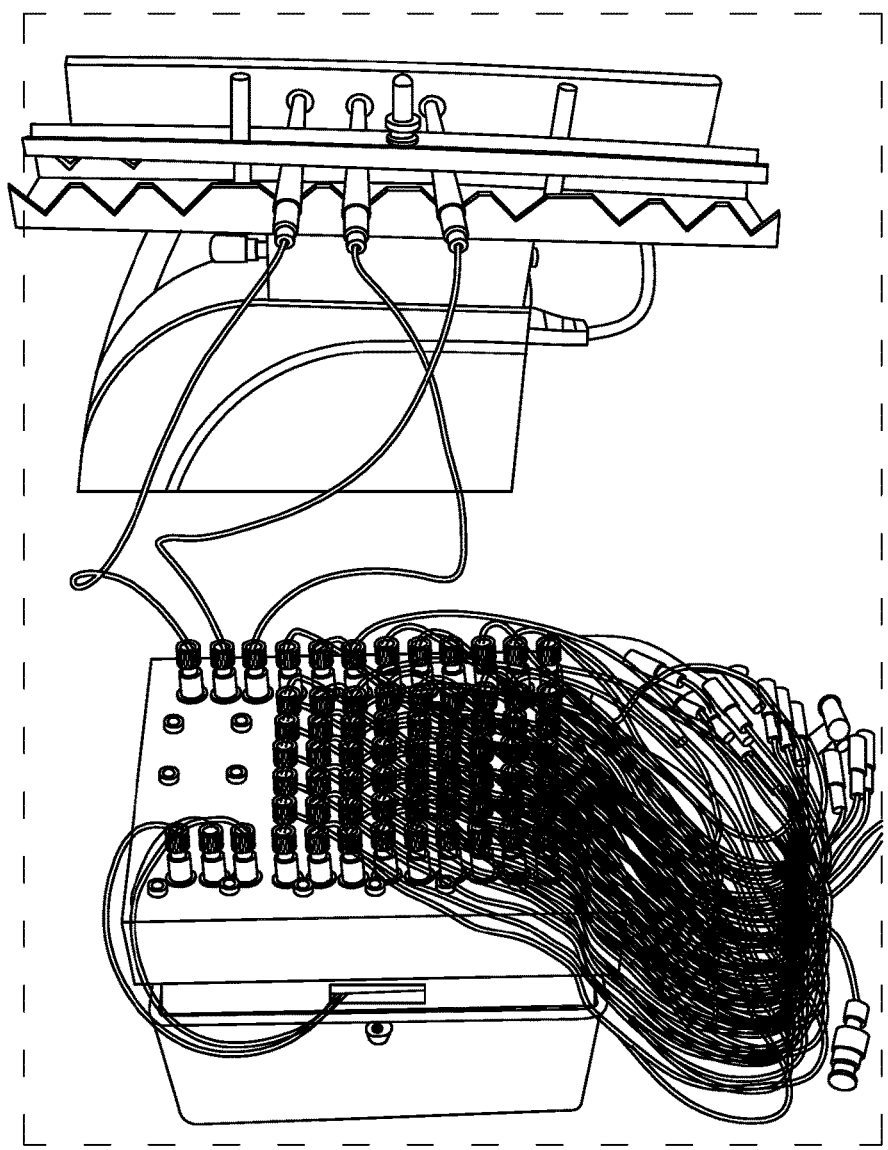
FIG. 31 is a photograph of aspects of microcolumn device of the present disclosure.
Figure 32:
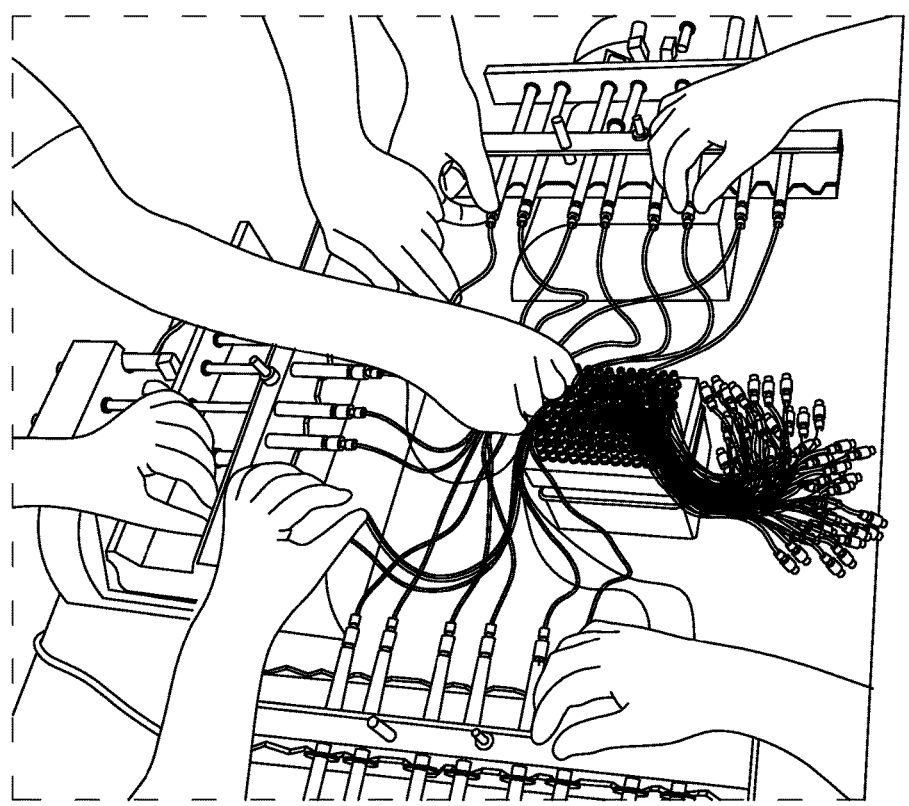
FIG. 32 is a photograph of aspects of microcolumn device of the present disclosure, illustrating the process of making connections to the device.
Figure 33:
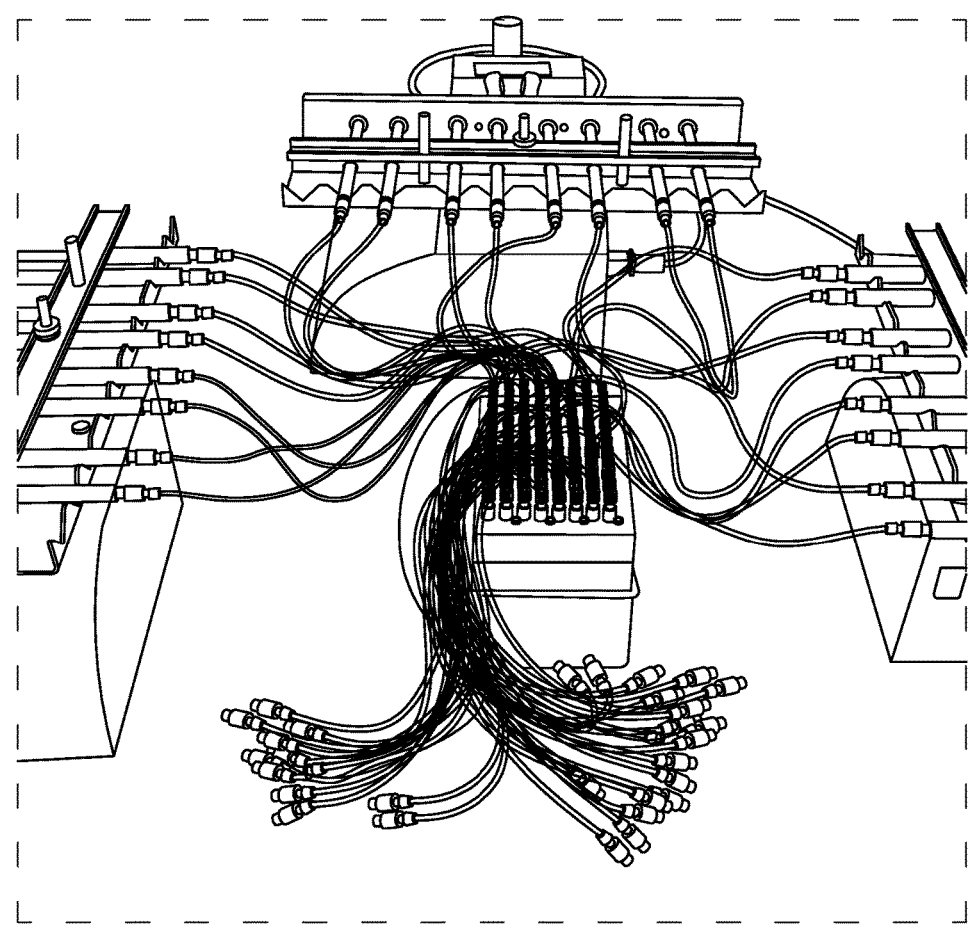
FIG. 33 is a photograph of aspects of microcolumn device system of the present disclosure, including illustrating a liquid flow mechanism (e.g., a pump).
Figure 34:
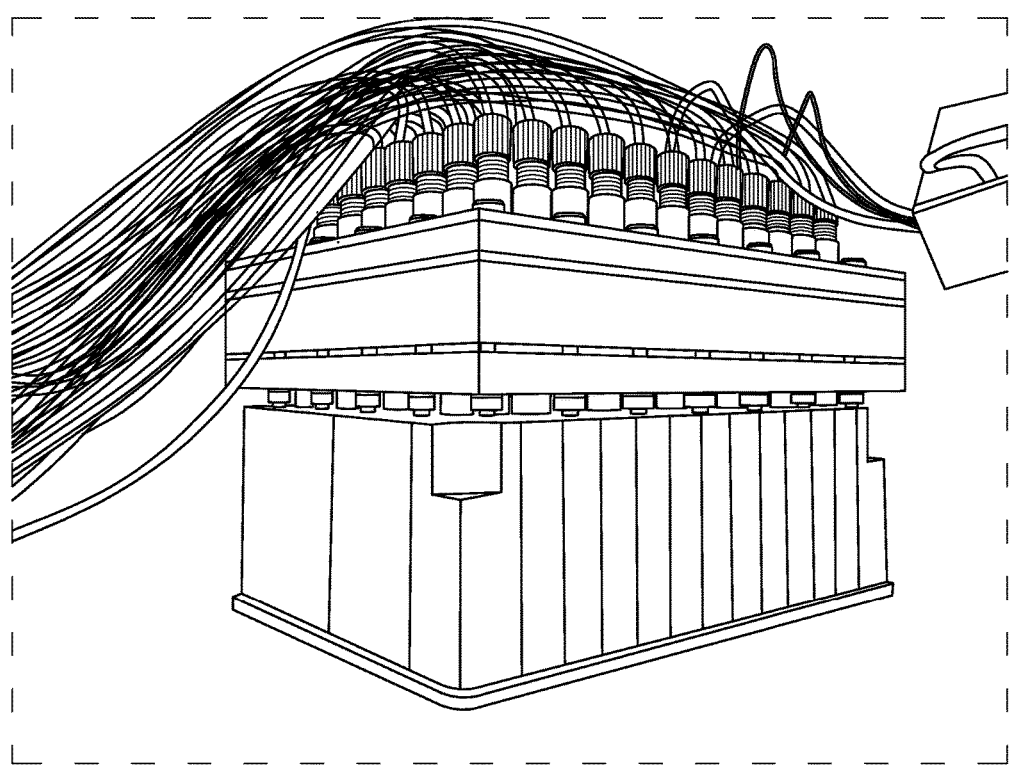
FIG. 34 is a photograph of a microcolumn device of the present disclosure.
Figure 35:
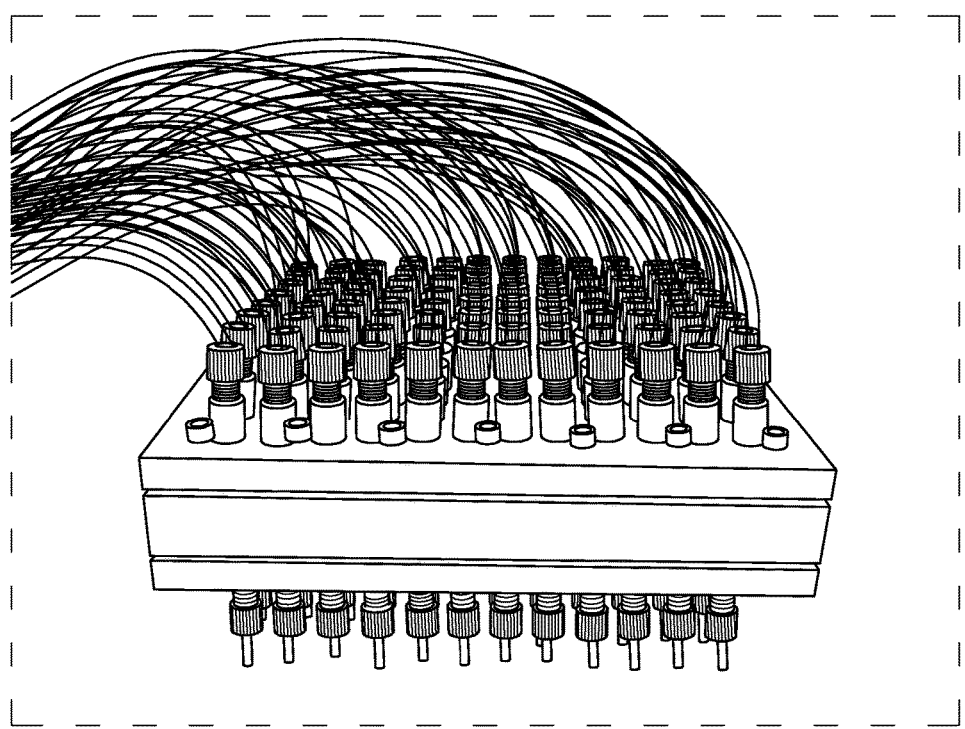
FIG. 35 is a photograph of a microcolumn device of the present disclosure.
Figure 36:
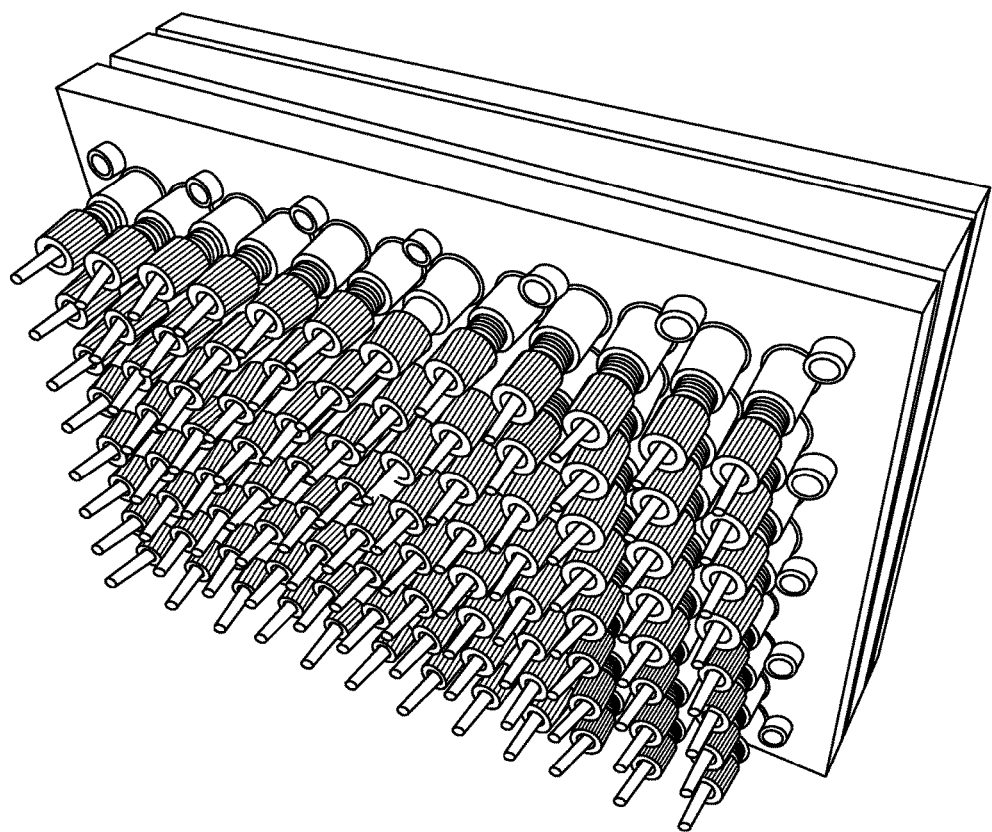
FIG. 36 is a photograph of aspects of a microcolumn device of the present disclosure.
Figure 37:
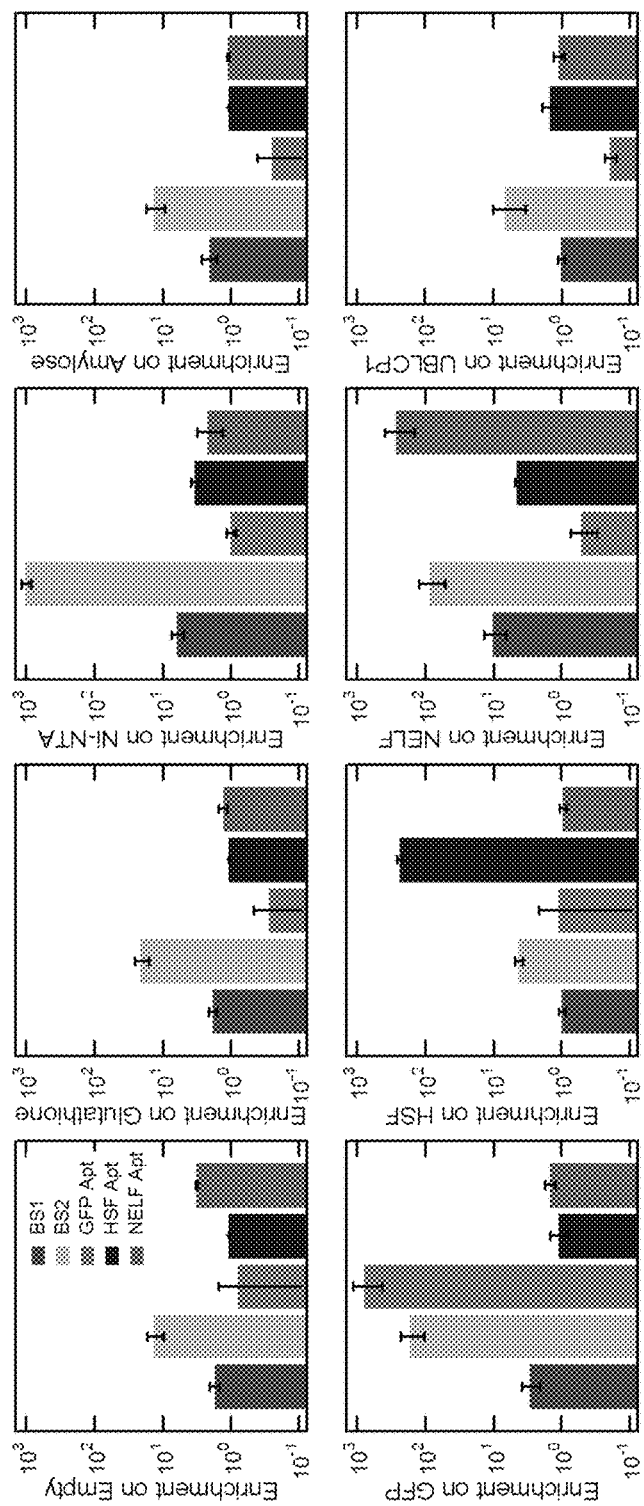
FIG. 37 is a graph illustrating test results of the use of one embodiment of a microcolumn device of the present disclosure.

FIGS. 29-37 illustrate additional embodiments of the device of the present disclosure and the operation and reconfiguration of the device. FIG. 29 illustrates a fluidic "ribbon" for use with the device of the present disclosure. FIG. 30 and FIG. 31 illustrate embodiments of the device of the present disclosure in serial configurations. FIG. 32 illustrates one embodiment of the device of the present disclosure in operation, and particularly showing the changing of the configuration of the device. FIG. 33 and FIG. 34 illustrate embodiments of the device of the present disclosure in parallel configuration during washing an elution into a 96 well plate. FIG. 35 and FIG. 36 illustrate embodiments of an isolated device of the present disclosure. FIG. 37 is a graph showing test results of the use of one embodiment of the device of the present disclosure in serial mode, where aptamers bind specifically to their target protein.

In various other embodiments, the device of the present disclosure can be made smaller than 96 well plate size to contain less columns. For example, other configurations can have 24, 48, or other well plate sizes.

EXAMPLES

The following examples are intended to illustrate particular embodiments of the present invention, but are by no means intended to limit the scope of the present invention.

Example 1

High-Throughput Binding Characterization of RNA Aptamer Selections Using a Microplate-Based Multiplex Microcolumn Device This example describes a versatile 96-well microplate-based device that utilizes affinity microcolumn chromatography to complement downstream plate-based processing in aptamer selections. This device is reconfigurable and is able to operate in serial and/or parallel mode with up to 96 microcolumns. We demonstrate the utility of this device by simultaneously performing characterizations of target binding using 5 RNA aptamers and a random library. This was accomplished through 96 total selection tests. Three sets of selections tested the effects of target concentration on aptamer binding compared to the random RNA library using aptamers to the proteins GFP, hHSF1, and NELF-E. For all three targets, we found significant effects consistent with steric hindrance with optimum enrichments at predictable target concentrations. In a fourth selection set, we tested the partitioning efficiency and binding specificity of our three proteins' aptamers, as well as two suspected background binding sequences, to 8 targets running serially. The targets included an empty microcolumn, three affinity resins, three specific proteins, and a non-specific protein control. The aptamers showed significant enrichments only on their intended targets. Specifically, the hHSF1 and NELF-E aptamers enriched over 200-fold on their protein targets, and the GFP aptamer enriched 750-fold. By utilizing our device's plate-based format with other complementary plate-based systems for all downstream biochemical processes and analysis, high-throughput selections, characterizations and optimization were performed to significantly reduce the time and cost for completing large scale aptamer selections.

To address various deficiencies in the field, a high-throughput device called MEDUSA (Microplate-based Enrichment Device Used for the Selection of Aptamers) was developed. This device is designed around a 96-well microplate format, which not only allows for high-throughput selections, but also complements existing plate-based methods and technologies for sample handling and has the potential for automation. MEDUSA is a substantial expansion of our previously reported modular and multiplexable microcolumns, which achieve non-equilibrium selections by utilizing dynamic flow rates shown to optimize the enrichment of aptamers (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85 (6):3417-3424). We demonstrate the use of MEDUSA by performing 96 simultaneous selection tests to characterize the binding of a number of RNA aptamers against various targets. In total, the characterization tests performed on MEDUSA shed light on the critical binding behaviors of specific and background binding aptamers that fundamentally limit the performance and sensitivity of solid-phase affinity selections.

Materials and Methods

Protein Immobilization on Affinity Resins:

Nickel-nitrilotriacetic acid (Ni-NTA) Superflow or glutathione-agarose (GSH) resins were extensively washed with binding buffer [10 mM N-2-hydroxyethylpiperazine-N'-ethanesulfonic acid (HEPES)-KOH pH 7.6, 125 mM NaCl, 25 mM KCl, 5 mM $MgCl_2$, and 0.02% Tween-20]. Hexahistidine- or GST-tagged proteins (see Table S1) were immobilized at the desired concentrations onto the washed resin in a 10% slurry with binding buffer and incubated at 4° C. with constant mixing for 1 hour.

RNA Library and Aptamers:

The random RNA library used in the experiments, hereafter referred to as N70 library, contains ~$5 \times 10^{15}$ sequences of 120-nucleotide (nt) RNA molecules and was prepared as described previously (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85 (6):3417-3424). This library consists of a 70-nt random region flanked by two constant regions. GFP-, hHSF1- and NELF-E-binding aptamers, GFPapt, HSFapt and NELFapt, as well as the background binding sequences (BBSs), BBS1 and BBS2, were all derived from previous multiplex SELEX experiments (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85 (6):3417-3424; Szeto K, Latulippe D R, Ozer A, Pagano J M, White B S, Shalloway D, Lis J T, Craighead H G (2013) RAPID-SELEX for RNA Aptamers. PloS one 8 (12):e82667; Shui B, Ozer A, Zipfel W, Sahu N, Singh A, Lis J T, Shi H, Kotlikoff M I (2012) RNA aptamers that functionally interact with green fluorescent protein and its derivatives. Nucleic Acids Res 40 (5):e39; Pagano J M, Kwak H, Waters C T, Sprouse R O, White B S, Ozer A, Szeto K, Shalloway D, Craighead H G, Lis J T (2014) Defining NELF-E RNA binding in HIV-1 and promoter-proximal pause regions. PLoS Genet 10 (1):e1004090). See Example 2 for details.

RNA Selections and Quantification:

For the sequence specificity study with serially configured microcolumns, each triplicate of 8 targets was exposed to 1 mL of a mixed RNA pool in binding buffer [4.75 nM N70 library, 50 pM GFPapt, 50 pM HSFapt, 50 pM NELFapt, 50 pM BBS1, 50 pM BBS2, and 10 μg/mL yeast tRNA (Invitrogen)]. Similarly for the protein concentration studies with parallel microcolumns, the mixed RNA pools consisted of 4.95 nM N70 library and 50 pM specific aptamer.

After binding to the library, the serially configured microcolumns were reconfigured to run in parallel. Each of the 96 microcolumns was then washed to remove unbound RNA. Finally, MEDUSA was placed directly onto a 2-mL 96-well microplate, and the RNA/RNA-protein complexes were eluted from the individual microcolumns. The RNA elution samples and the input standards were phenol/chloroform-extracted and ethanol-precipitated and the pools and standards were reverse transcribed in two 96-well microplates. Each of the cDNA products was used for quantitative PCR (qPCR) analysis using 384-well plates on a LightCycler 480 instrument (Roche) to determine the amount of RNA library and of each specific aptamer that was recovered from each microcolumn. Different sets of oligonucleotides were used to independently evaluate the amount of N70 library and specific aptamers in each pool. See Supplementary Material for details.

Design and Fabrication of MEDUSA:

MEDUSA was modeled after a 96-well microplate. The 96 units of our device were based off of our previously reported modular and mutliplexable affinity microcolumns, which were shown to minimize reagent consumption while demonstrating significantly improved performances through optimizations of the selection parameters (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85 (6):3417-3424). In order to allow for simple and versatile multiplexing and connectivity between microcolumns, our device was designed to be assembled in layers, with some of the layers "programed" for establishing connections within the device (see FIG. 1 and Example 2 for more details). To fabricate the layers of MEDUSA, a two-dimensional CAD for each layer was designed and then cut using a $CO_2$ laser at 10.6 μm (Universal Laser Systems VersaLaser). The speed, intensity, and density of laser pulses were optimized for each layer to obtain the highest quality and most reproducible cuts.

Results and Discussion

Figure 38:
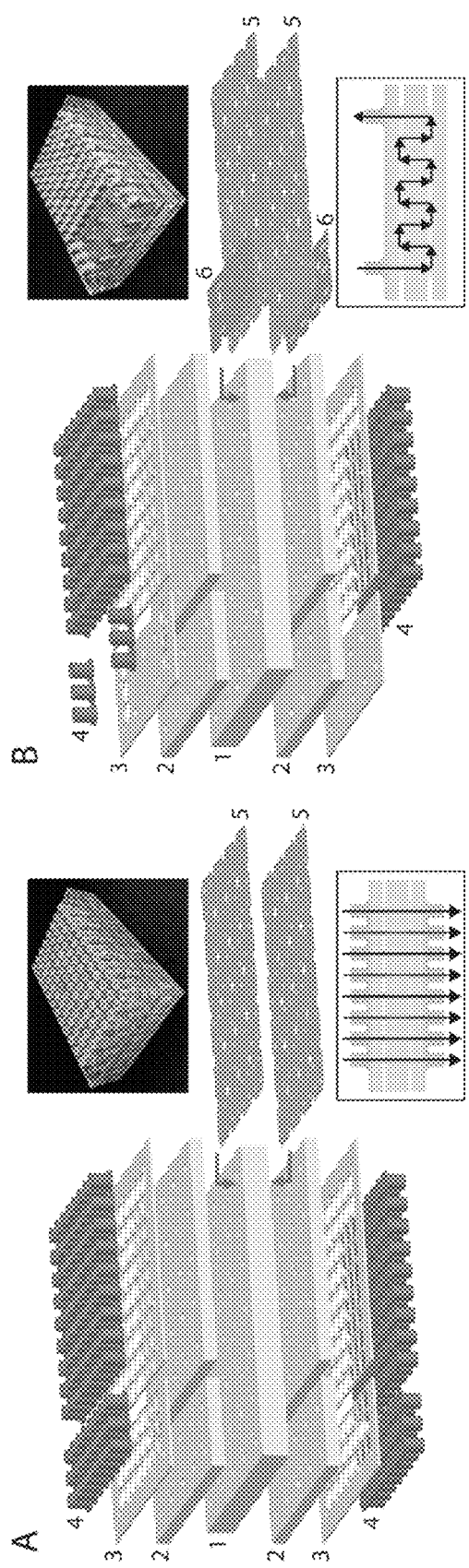
FIGS. 38A-38B are schematics illustrating layers of a microcolumn device (i.e., MEDUSA) in the order of assembly.

MEDUSA as an Adaptable Platform:

MEDUSA was designed for high-throughput aptamer selections and characterizations of the SELEX process, and for versatility, allowing any combination of serial and parallel experiments. Due to the availability of plate-based processes and the potential for automation, we designed our device using the standard 96-well microplate layout, which easily couples with a typical 96-well plate for further post-selection sample processing. Furthermore, laser cutting MEDUSA was ideal for rapid prototyping, requiring only 1 hour to machine each device. For a universal device that does not necessitate customized plastic layers, a third layer of silicone could be used to similarly program the accessibility of all 96 possible input and output ports to the microcolumns. However, due to the inexpensive and rapid fabrication methods used, we decided instead to fabricate custom capping and washer layers that relay the same flow program by containing only the necessary input/output holes and NanoPorts. For the 3 sets of 8 serialized microcolumns shown, this required only 6 holes/ports on the top layers and none on the bottom layers. This configuration also allowed for visual assessment of solutions flowing through the serialized microcolumns. The ease of fabrication for different programmed parts, especially in thin silicone, allows for customized and versatile selections that can contain any number of parallel or serially-connected microcolumns, as well as utilizing both configurations simultaneously. In cases where more than 96 microcolumns are desired, such as when 96 targets each require negative selections, additional microcolumn layers can be utilized in the assembly. As illustrated, our device was fabricated to accommodate 3 sets of 8 serialized devices, as well as 72 parallel selections (FIGS. 38A-38B). This combination was easily programmed as described above. However, an even greater degree of versatility was achieved by dividing the capping, washer, and programmed silicone layers into separately fabricated subsections that could be individually addressed and reconfigured without disrupting other microcolumns. This strategy also suggests the possibility of fabricating smaller versions of MEDUSA that contain the same general layout of a microplate, but occupy a smaller footprint by utilizing fewer microcolumns. This would allow users to handle smaller devices in less demanding applications, while benefiting from the standardized spacing and addressability of plate-based selections and sample processing.

Figure 41:
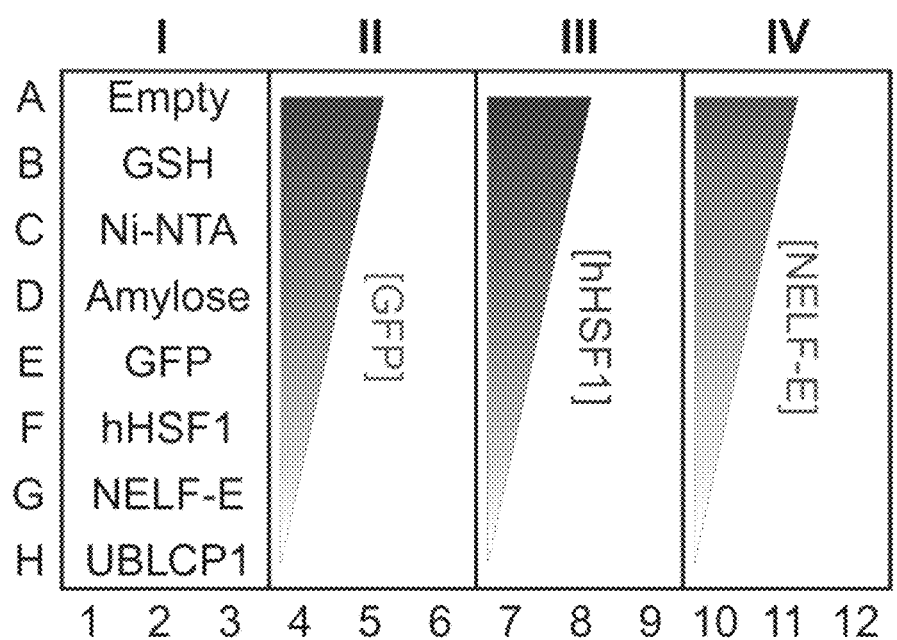
FIG. 41 is a graph illustrating the layout for the 96 targets on MEDUSA according to its analogous microplate position given by the rows A-H, and the columns 1-12. In section I, the 8 indicated targets were connected in series from A to H to test the specificity and partitioning efficiency of various RNA aptamers. This was tested in triplicate in columns 1 to 3. Sections II, III, and IV tested the effects of target surface concentration on aptamer enrichments. The colored triangles indicate decreasing concentrations of each protein from 10 µg/µL (row A) to 0.016 µg/µL (row H) in 2.5-fold dilutions. Section II (green triangle) aimed to confirm previous enrichment behaviors shown with GFP. Sections III and IV tested the same concentrations of the proteins hHSF1 (blue triangle) and NELF-E (red triangle) to assess the prevalence of target surface concentration effects on binding due to steric hindrance or other effects in other aptamer selections.

Parallel Selections Reveal Critical Target Concentration for Aptamer Enrichments:

In our previous work, we found that GFP aptamer enrichments were limited by a critical GFP concentration that we attributed to steric hindrance (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85 (6):3417-3424). Using MEDUSA, we decided to reproduce the GFP results with more data points, and to investigate the prevalence of this limiting effect by performing analogous studies with two additional proteins, hHSF1 and NELF-E, and their respective aptamers, HSFapt and NELFapt (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85 (6):3417-3424; Pagano J M, Kwak H, Waters C T, Sprouse R O, White B S, Ozer A, Szeto K, Shalloway D, Craighead H G, Lis J T (2014) Defining NELF-E RNA binding in HIV-1 and promoter-proximal pause regions. PLoS Genet 10 (1):e1004090). For each protein target, we chose to test 8 concentration conditions starting at 10 µg/µL of resin with 2.5-fold dilutions down to 0.016 µg/µL in triplicate. The layout for all the samples on MEDUSA is illustrated in FIG. 41 in the sections denoted II, III, and IV.

Figure 39:
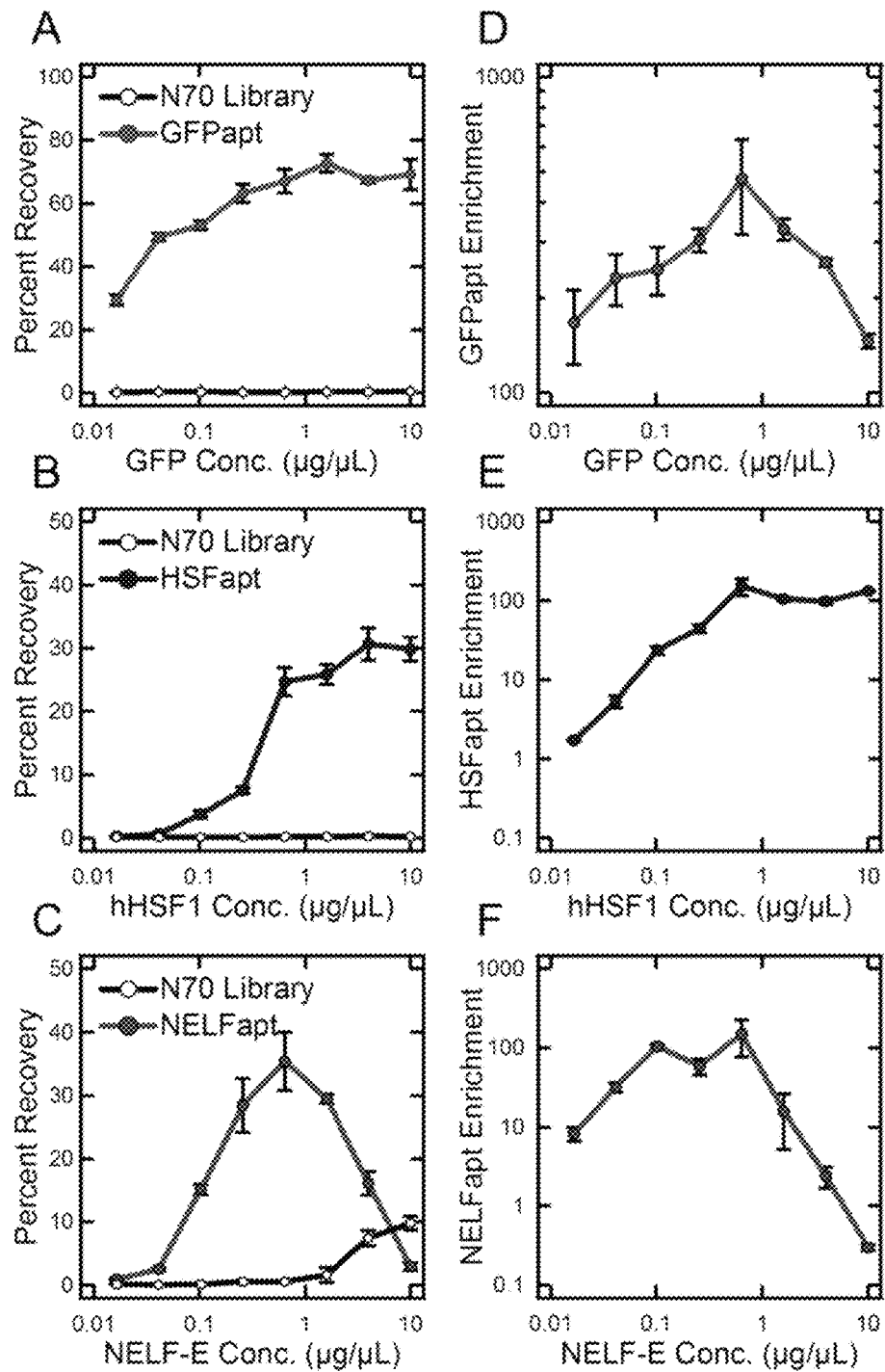
FIGS. 39A-39F are graphs illustrating recoveries and enrichments of specific RNA aptamers over the N70 library as a function of protein concentration.

The binding results and enrichments for all three proteins are shown in FIG. 39. The GFP microcolumns recovered a higher percentage of GFPapt and a lower percentage of N70 library than those reported previously (FIG. 39A), due to lower flow rates that were used to increase HSFapt and NELFapt binding, since they have higher $K_d$s. This resulted in an expected increase in the enrichment of GFPapt over the N70 library; however, the characteristic shape and optimal concentration of 0.6 µg/µL for the enrichment curve are the same as previously reported (FIG. 39D). With hHSF1, the recovery of HSFapt followed a more typical sigmoidal shape, which saturated at increasing concentrations of hHSF1 (FIG. 39B). Similarly, the enrichment of HSFapt over the N70 library increased steadily and then saturated at higher concentrations (FIG. 39E). It is interesting, however, that HSFapt enrichment plateaued at the optimal concentration for GFP. With NELF-E, there is a very clear NELFapt recovery optimum at this same concentration, with significant losses in recoveries at concentrations above 0.6 µg/µL (FIG. 39C). In addition, the recovery of the N70 library increased significantly above the optimum concentration for NELFapt, likely due to the fact that NELF-E contains an RNA Recognition Motif (RRM) and can bind RNA non-specifically (Pagano J M, Kwak H, Waters C T, Sprouse R O, White B S, Ozer A, Szeto K, Shalloway D, Craighead H G, Lis J T (2014) Defining NELF-E RNA binding in HIV-1 and promoter-proximal pause regions. PLoS Genet 10 (1): e1004090). These two binding trends result in a drastic decrease in enrichment at higher concentrations of NELF-E, resulting in de-enrichment of NELFapt at the highest concentration of 10 µg/µL (FIG. 39F).

The three concentration studies with GFP, hHSF1 and NELF-E make a strong case for the general steric hindrance of target molecules that are over packed in solid-phase affinity selections. Although the GFP and hHSF1 aptamer recoveries do not show drastic decreases at high concentrations as with NELF-E, this binding behavior is affected by the selection flow rates and is clearly seen between our old and new GFP data. Importantly, the recoveries saturated well below 100%, which indicates the existence of some limiting effect. Most revealing is NELF-E, where the binding site for NELFapt appears to be particularly inaccessible at high concentrations, causing a significant loss in total aptamer binding. Furthermore, a simple calculation (assuming hard spheres for the resin) predicts that a critical surface density of proteins should occur between 0.1 and 1 µg/µL (depending on protein shape and size and the diameter of the resin beads). Since all three proteins are similar in size, it is not surprising that we observe the same critical concentration of 0.6 µg/µL, and the results suggest that the target concentration may be the most limiting parameter for enriching aptamers.

Multiplex Serial Selections Show Specificity of Target and Background Binding Sequences:

In previous work, we performed multiple partitions to input pools and libraries by connecting several microcolumns in multiplex selections (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85 (6):3417-3424). In particular, we showed the highly specific and efficient partitioning of GFPapt to GFP over non-specific proteins and an empty microcolumn. This configuration is useful for multi-tasking DNA or RNA libraries on multiple unrelated selection targets, or to separate enriched pools for aptamers that bind to distinct sites on a complex target (Gong Q, Wang J P, Ahmad K M, Csordas A T, Zhou J H, Nie J, Stewart R, Thomson J A, Rossi J J, Soh H T (2012) Selection Strategy to Generate Aptamer Pairs that Bind to Distinct Sites on Protein Targets. Analytical chemistry 84 (12):5365-5371). We decided to demonstrate similar multiplex selections using MEDUSA by extending this analysis to include several additional RNA aptamers and protein targets: GFP, hHSF1, NELF-E and their respective aptamers. To thoroughly characterize the specific, non-specific, and background binding of each RNA aptamer, we also included a non-specific protein, UBLCP1, three commonly used affinity resins, GSH, Ni-NTA, and Amylose, and empty microcolumns. Each of the four protein targets were immobilized onto their respective resins at 0.6 µg/µL. The 8 targets were arranged in series for the multiplex selection and performed in triplicate to quantify the reproducibility of each aptamer's partitioning efficiency and specificity. The order of targets was as follows: Empty, GSH, Ni-NTA, Amylose, His-GFP, GST-hHSF1, His-NELF-E, His-UBLCP1, and is illustrated in FIG. 41 in section I.

In addition to the random N70 RNA library and the aptamers to our three proteins, our test pool also included two suspected BBSs, BBS 1 and BBS2. For all previous multiplex selections, we have performed high-throughput sequencing, which provided tremendous amounts of sequence data and sensitivity for early detection of aptamers (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85 (6):3417-3424; Szeto K, Latulippe D R, Ozer A, Pagano J M, White B S, Shalloway D, Lis J T, Craighead H G (2013) RAPID-SELEX for RNA Aptamers. PloS one 8 (12): e82667; Pagano J M, Kwak H, Waters C T, Sprouse R O, White B S, Ozer A, Szeto K, Shalloway D, Craighead H G, Lis J T (2014) Defining NELF-E RNA binding in HIV-1 and promoter-proximal pause regions. PLoS Genet 10 (1): e1004090). However, comparison of the sequencing results for dozens of targets revealed several identical sequences that were frequently enriched, particularly in earlier cycles before target-binding aptamers began to dominate the pool. This was especially true for less aptagenic targets, where the two sequences, BBS1 and BBS2, were generally among the highest enriched candidates (see Table 2). From these data, we predicted that BBS1 would enrich on all targets by binding to the plastic device and the resins. This was also predicted for BBS2; however, we expected BBS2 to enrich more strongly than BBS1 on all targets, especially in microcolumns containing Ni-NTA (similar analyses have been used to identify sequences that bind specifically to Ni-NTA (Nastasijevic B, Becker N A, Wurster S E, Maher L J, 3rd (2008) Sequence-specific binding of DNA and RNA to immobilized Nickel ions. Biochem Biophys Res Commun 366 (2):420-425)).

Figure 40:
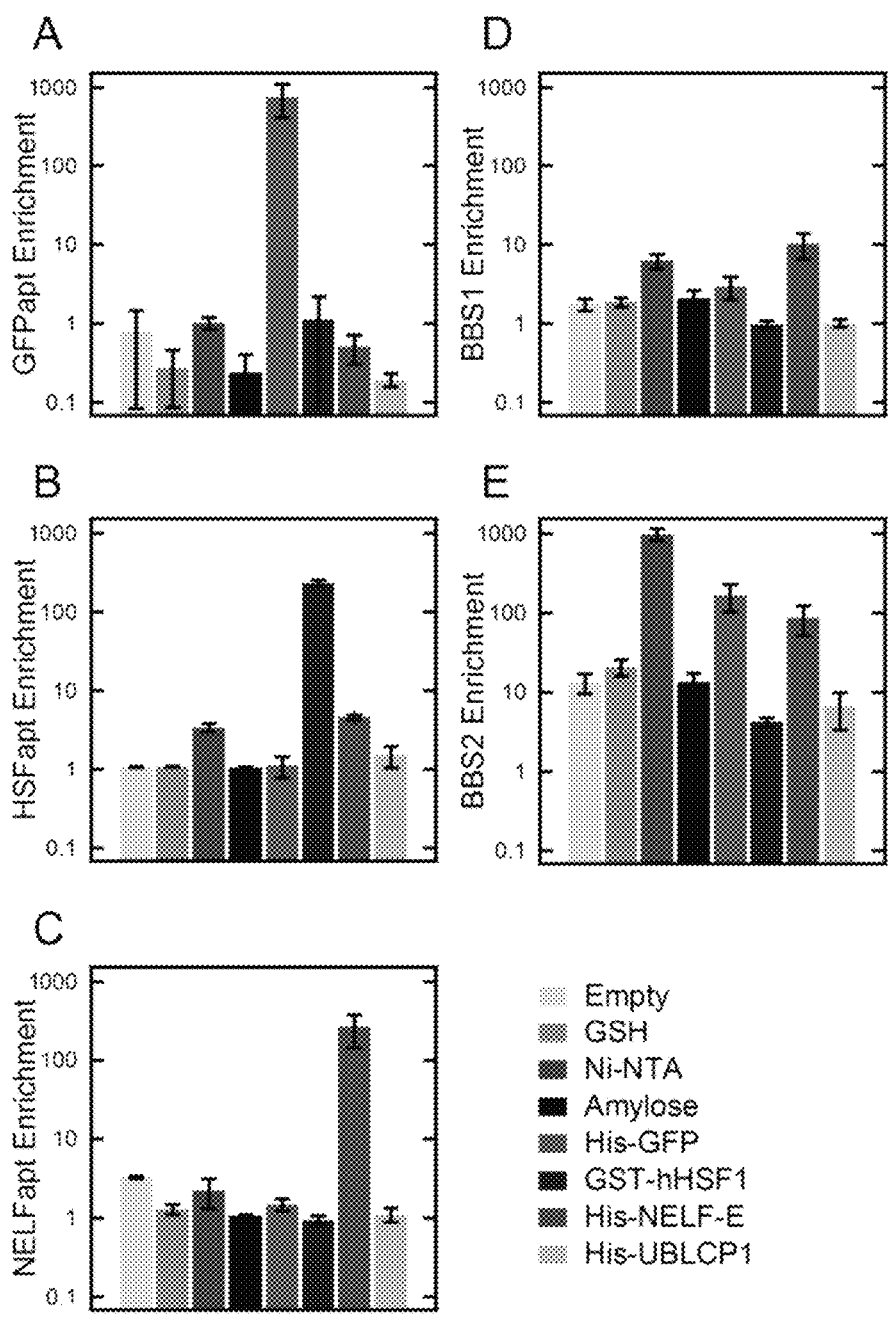
FIGS. 40A-40E are graphs illustrating the enrichment of RNA aptamers over the N70 library on various targets connected in series. The enrichment of each protein-specific aptamer, GFPapt (FIG. 40A), HSFapt (FIG. 40B), and NELFapt (FIG. 40C), and non-specific aptamers, BBS1 aptamer (FIG. 40D), and BBS2 aptamer (FIG. 40E), on all 8 microcolumns. The error bars represent the standard deviation in enrichments calculated for each target performed in triplicate.

The partitioning results for each RNA aptamer are shown in FIG. 40 as enrichments over the random RNA library. Our specific aptamers each show striking enrichments only on their intended target. GFPapt enriched an average of 750-fold on GFP microcolumns, but only an average of 0.6-fold (de-enriched) on all other targets (FIG. 40A), which reflects its strong specificity for GFP. Similarly, HSFapt enriched an average of 232-fold on hHSF1 microcolumns, and only an average of 2-fold on all other targets (FIG. 40B). NELFapt enriched an average of 262-fold on NELF-E, and only an average of 1.6-fold for all other targets (FIG. 40C).

For BBS1 and BBS2, we found good agreement with the qualitative analysis of all previous sequencing data (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85 (6):3417-3424; Szeto K, Latulippe D R, Ozer A, Pagano J M, White B S, Shalloway D, Lis J T, Craighead H G (2013) RAPID-SELEX for RNA Aptamers. PloS one 8 (12):e82667; Pagano J M, Kwak H, Waters C T, Sprouse R O, White B S, Ozer A, Szeto K, Shalloway D, Craighead H G, Lis J T (2014) Defining NELF-E RNA binding in HIV-1 and promoter-proximal pause regions. PLoS Genet 10 (1):e1004090). BBS1 enriched on all targets as predicted; however, it enriched 3 times more in Ni-NTA-containing microcolumns (Ni-NTA, GFP, NELF-E, UBLCP1), with enrichments averaging 1.7 for non-Ni-NTA targets and 5.1 for the Ni-NTA targets (FIG. 40D). BBS2 also enriched as predicted, with enrichments higher than BBS1 on all targets (FIG. 40E). More specifically, BBS2 enriched an average of 13-fold on non-Ni-NTA targets and a surprising 311-fold on Ni-NTA targets suggesting that BBS2 has a specific affinity for Ni-NTA. In fact, for the first Ni-NTA target in the serial selection, blank Ni-NTA, enrichment averaged almost 1000-fold. This is almost 80 times greater than non-Ni-NTA targets, and may reflect more accurately the specificity of BBS2 for Ni-NTA. In support of this hypothesis, we noticed that BBS2 was quickly depleted from the pool as it was injected across all the Ni-NTA-containing microcolumns, as seen by the monotonically decreasing enrichments of BBS2 to the Ni-NTA-containing targets from left to right.

Although negative selections are often used to separate sequences with specific affinities for sources of background binding, these are rarely completely effective at eliminating enrichment of non-specific RNAs. In contrast, we have found the repeated occurrence of BBSs in different SELEX experiments to be valuable indicators of the selection progress. Perhaps more interestingly, selections for and/or identification of BBSs can be used to generate non-specific blocking reagents that are more effective than commonly used yeast tRNAs.

Conclusions

It is believed that MEDUSA can be used to significantly increase the productivity of large-scale aptamer discovery efforts. By utilizing the versatility and programmability of MEDUSA, a larger configuration space of potential SELEX designs can be explored. Just as importantly, selections utilizing affinity chromatography can be thoroughly characterized. These kinds of data not only allow us to optimize future aptamer selections, but also clearly show that performances can be improved, while simultaneously consuming much less reagent, such as protein, making aptamer selections more accessible to targets that are difficult to purify or express in large quantities. Furthermore, such characterizations would not only improve future aptamer selections, but also aid in the development of more functional and applicable SELEX theories in solid-phase affinity selections.

Example 2

Supplementary Material

High-Throughput Binding Characterization for RNA Aptamers Selections Using a Microplate-Based Multiplex Microcolumn Device Preparation of Recombinant Protein Targets:

Recombinant proteins were expressed in BL21(DE3)-RIPL E. coli cells (Agilent Technologies) transformed with plasmids that encode for hexahistidine-tagged GFP, Drosophila NELF-E, and UBLCP1, or GST-tagged hHSF1 (Table 1). Two or four liter LB cultures supplemented with 100 μg/mL ampicillin were inoculated with starter LB culture derived from a single colony and grown at 37° C. until the OD600 reached approximately 0.6. Protein expression was induced by the addition of IPTG to a final concentration of 1 mM. After an additional incubation, bacteria were collected by centrifugation and the resulting pellet was processed according to the manufacturer's instructions for Ni-NTA Superflow (Qiagen) or Glutathione-agarose (Thermo Scientific) resins. SDS-polyacrylamide gel electrophoresis (SDS-PAGE) was used to verify the purity and quality of the final protein product. Resulting protein preps were dialyzed against 1×PBS (supplemented with 5 mM 2-mercaptoethanol and 0.01% Triton X-100) and stored in small aliquots after addition of glycerol to a final concentration of 20%. NELF-E was prepared slightly differently (Pagano J M, Kwak H, Waters C T, Sprouse R O, White B S, Ozer A, Szeto K, Shalloway D, Craighead H G, Lis J T (2014) Defining NELF-E RNA Binding in HIV-1 and Promoter-Proximal Pause Regions. PLoS Genetics 10:e1004090).

Nucleic Acid Library, Protein- and Background-Binding Aptamers:

The random N70 library, contains ~5×10$^{15}$ sequences of 120-nucleotide (nt) RNA molecules and was prepared as described previously (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85:3417-3424). This library consists of a 70-nt random region flanked by two constant regions. HSFapt was previously identified as hHSF2-R5-2 using the N70 library and characterized elsewhere (Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85:3417-3424). NELFapt was previously identified as Napt1 using the N70 library (Pagano J M, Kwak H, Waters C T, Sprouse R O, White B S, Ozer A, Szeto K, Shalloway D, Craighead H G, Lis J T (2014) Defining NELF-E RNA Binding in HIV-1 and Promoter-Proximal Pause Regions. PLoS Genetics 10:e1004090). The background binding sequences BBS1 and BBS2 were identified in several previous multiplex SELEX experiments using the N70 library for dozens of target proteins (Pagano J M, Kwak H, Waters C T, Sprouse R O, White B S, Ozer A, Szeto K, Shalloway D, Craighead H G, Lis J T (2014) Defining NELF-E RNA Binding in HIV-1 and Promoter-Proximal Pause Regions. PLoS Genetics 10:e1004090; Latulippe D R, Szeto K, Ozer A, Duarte F M, Kelly C V, Pagano J M, White B S, Shalloway D, Lis J T, Craighead H G (2013) Multiplexed microcolumn-based process for efficient selection of RNA aptamers. Analytical chemistry 85:3417-3424; Szeto K, Latulippe D R, Ozer A, Pagano J M, White B S, Shalloway D, Lis J T, Craighead H G (2013) RAPID-SELEX for RNA Aptamers. PloS one 8:e82667). The GFP-binding RNA aptamer, GFPapt, used in this work was selected using a different library with a smaller random region and different constant regions; and was previously identified as AP3-1 (Shui B, Ozer A, Zipfel W, Sahu N, Singh A, Lis J T, Shi H, Kotlikoff M I (2012) RNA aptamers that functionally interact with green fluorescent protein and its derivatives. Nucleic Acids Res 40:e39).

The 84-nt GFP-binding RNA aptamer has the following sequence: 5'-AGCUUCUGGACUGCGAUGGGAGCAC-GAAACGUCGUGGCGCAAUUGGGUGGGG AAAGU-CCUUAAAAGAGGGCCACCACAGAAGCU-3' (SEQ ID NO:1). The forward and reverse oligos used for qPCR analyses were GFPapt-FOR: 5'-GCTTCTGGACTGC-GATGGGAGCA-3' (SEQ ID NO:2) and GFPapt-REV: 5'-GCTTCTGTGGTGGCCCTCTTTTAAGGACT-3' (SEQ ID NO:3).

The 117-nt hHSF1-binding RNA aptamer has the following sequence: 5'-<u>GGGAAUGGAUCCACAUCUACGA-AUUC</u>AAUCAAGUCCCAGACUCAGCAACACUGG-ACAGCGAUAUGCAGAUAACCAAGACCAAUUCAC-UCCAG<u>UUCACUGCAGACUUGACGAAGCUU</u>-3' (SEQ ID NO:4). The two constant regions corresponding to the library design are denoted by underlines. The forward and reverse oligos used for qPCR analyses were HSFapt-FOR: 5'-AATCAAGTCCCCAGACTCAGCAACA-3' and HSFapt-REV: 5'-CTGGAGTGAATTGGTCTTGGTTATC-3' (SEQ ID NO:5).

The 120-nt NELF-E-binding RNA aptamer has the following sequence: 5'-<u>GGGAAUGGAUCCACAUCUAC-GAAUUC</u>CCAACGACUGCCGAGCGAGAUUACGCU-UGAGCGCCCACUGAGGAUGCCCACGGGCGAUU-GGGGCACGG<u>UUCACUGCAGACUUGACGAAGCU-U</u>-3' (SEQ ID NO:6). The two constant regions corresponding to the library design are denoted by underlines. The forward and reverse oligos used for qPCR analyses were NELFapt-FOR: 5'-CCAACGACTGCCGAGCGAGAT-TAC-3' and NELFapt-REV: 5'-GCCGTGCCCCAATCGC-CCGTG-3' (SEQ ID NO:7).

BBS1 has the following sequence: 5'-<u>GGGAAU-GGAUCCACAUCUACGAAUUC</u>CGCAGGGCUAGCC-GCAUGCUCAGGCCUGGCGGGUAGGGAGUUAGGG-UAGGGAGACCAGGAGAGCUGGC<u>UUCACUGCAGA-CUUGACGAAGCUU</u>-3' (SEQ ID NO:8). The forward and reverse oligos used for qPCR analyses were BBS1-FOR: 5'-CGCAGGGCTAGCCGCATG-3' (SEQ ID NO:9) and BBS1-REV: 5'-GCCAGCTCTCCTGGTCTCC-3' (SEQ ID NO:10).

BBS2 has the following sequence: 5'-<u>GGGAAU-GGAUCCACAUCUACGAAUUC</u>CGAAGCUCGUGAC-GGUACCUCCUAAAAUGUCCAUGGGGAAGGGAGG-GAAUGGGAAGGACAAUCGGACACCG<u>UUCACUGC-AGACUUGACGAAGCUU</u>-3' (SEQ ID NO:11). The forward and reverse oligos used for qPCR analyses were BBS2-FOR: 5'-CGAAGCTCGTGACGGTACC-3' (SEQ ID NO:12) and BBS2-REV: 5'-CGGTGTCCGATTGTCCTTC-3' (SEQ ID NO:13).

The N70 library forward and reverse oligos used for qPCR analyses were Lib-FOR oligo: 5'-GATAATACGACT-CACTATAGGGAATGGATCCACATCTACGA-3' (SEQ ID NO:14) and Lib-REV oligo: 5'-AAGCTTCGTCAAGTCT-GCAGTGAA-3' (SEQ ID NO:15).

All of the oligos used in this work were obtained from Integrated DNA Technologies.

Preparation of Protein- and Background-Binding Aptamers:

Sequence verified DNA templates for each one of the specific aptamers used in this study were transcribed using T7 RNA Polymerase. After transcription, the samples were treated with DNase I (Ambion), PAGE-purified, phenol:chloroform and chloroform extracted, isopropanol precipitated, and then re-suspended in DEPC-treated $H_2O$.

TABLE 1

Properties of the target proteins

| Protein | Molecular Weight (kDa) | Isoelectric Point | Affinity tag |
|---|---|---|---|
| GFP | 27 | 5.5 | Hexahistidine (n-terminus) |
| hHSF1 | 86 | 5.3 | GST* (n-terminus) |
| NELF-E | 36 | 8.9 | Hexahistidine (n-terminus) |
| UBLCP1 | 37 | 6.1 | Hexahistidine (c-terminus) |

*GST tag ~30 kDa

RNA Selections and Quantification:

The RNA pools were injected at a rate of 33 µL/min for 30 min with a 10 µL aliquot of each pool set aside and used as a standard for quantitative polymerase chain reaction (qPCR) analysis. All buffers and solutions were degassed prior to use and introduced into the microcolumns via programmable multichannel syringe pumps (Harvard Apparatus) with MEDUSA placed onto a 96-well format liquid waste reservoir. The microcolumns were reconfigured to run in parallel by removing the caps and silicone layers permitting the connectivity of microcolumns, and reassembling the device with the appropriate caps for a parallel configuration, and washed with 3 mL of binding buffer at a rate of 300 µL/min. The RNA/RNA-protein complexes were eluted directly into a 96-well microplate from the individual microcolumns by flowing elution buffer [binding buffer+50 mM ethylenediaminetetraacetic acid (EDTA pH 8.0) for selections with Ni-NTA resin; binding buffer+10 mM glutathione for selections with GSH resin; binding buffer+10 mM maltose for selections with amylose-resin] at a rate of 50 µL/min for 12 min. Samples and standards were phenol/chloroform-extracted and ethanol-precipitated together with 1 µL of GlycoBlue (Ambion) and 40 µg of yeast tRNA (Invitrogen), and the resulting pellet was resuspended in 20 µL of RNase-free water, and reverse transcribed with Moloney Murine Leukemia Virus Reverse Transcriptase (MMLV-RT) in two 96-well microplates. The N70 library, HSFapt, NELFapt, BBS1, and BBS2 all contain the same 3' constant region and were reverse transcribed using Lib-REV primer complementary to the 3' constant region in the RNA. For the experiments containing GFPapt, 4 µL of the resuspended pools and the standards were reverse transcribed using the GFPapt-REV primer specific to GFPapt. A 10-µL volume of each of the cDNA products was used for qPCR analysis using 384-well plates on a LightCycler 480 instrument (Roche) to determine the amount of RNA library and of each specific aptamer that was recovered from each microcolumn. Different sets of oligonucleotides (see above) were used to independently evaluate the amount of N70 library and specific aptamers in each pool.

Descriptions of MEDUSA's Components:

Each layer of MEDUSA was fabricated from either transparent biocompatible poly(methyl methacrylate) (PMMA) plastic or silicone. As seen in FIG. 38A (lower boxed inset), for parallelized microcolumns, there are 5 layers of plastic and 2 layers of silicone as well as NanoPorts (IDEX Health and Science) for inputs and outputs on each side. The center most plastic layer (number "1" in FIG. 38A) is ½" thick and contains 96 microcolumns that each hold 10 µL of total volume. The next pair of layers (numbered "5" in FIG. 38A above and below the microcolumns) are 1/16" silicone layers for making a liquid tight seal across all 96 microcolumns. These layers contain 2 mm diameter holes for inserting porous polyethylene frits above and below each microcolumn to retain target-bound affinity resins, and have adhesive on one side for bonding to the microcolumn layer. The next pair of layers (numbered "2" in FIG. 38A) are ¼" plastic capping layers which have small holes and NanoPorts (numbered "4") bonded around them to allow solutions to flow in and out of the microcolumns. The outer most plastic layers (numbered "3" in FIG. 38A) are 1 mm thick and designed to simultaneously aid the alignment of the Nano-Ports to the capping layers, as well as to bear and distribute forces from the assembly of all the layers by acting as a washer. All of the layers contain 35 evenly-spaced holes, with the middle microcolumn layer being threaded, for sealing the device together with screws (FIGS. 38A and 38B upper inset photographs). For serialized microcolumns (FIG. 38B, lower boxed inset), the design and assembly is similar. However, there are 2 additional layers of silicone (numbered "6" in FIG. 38B). These layers are fabricated in 1/32" silicone (no adhesive) and are programmed to allow for the connectivity of microcolumns through small interconnecting channels.

Table 2 provides a summary of the number of times BBS1 or BBS2 has been identified in all previous selections. The numbers indicate the instances in which BBS 1 was more highly enriched than BBS2 (or vice versa) on each target, grouped according to the resin on which each target was immobilized.

TABLE 2

Frequencies of BBS1 and BBS2 in Previous Selections

| Resin | BBS1 Dominant | BBS2 Dominant |
| --- | --- | --- |
| Ni-NTA | 1 | 7 |
| GSH | 3 | 4 |
| Amylose | 3 | 4 |
| Empty (no Resin) | 0 | 2 |

All references cited herein are incorporated herein by reference in their entirety and for all purposes to the same extent as if each individual publication, patent or patent application was specifically and individually indicated to be incorporated by reference in its entirety for all purposes.

Citation of a reference herein shall not be construed as an admission that such reference is prior art to the present invention. All references cited herein are hereby incorporated by reference in their entirety.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A device for conducting affinity chromatography in multiple microcolumns in parallel and/or in series, said device comprising:
a microcolumn layer comprising a top surface, a bottom surface, and a plurality of vertically aligned microcolumns for passing one or more sample liquids therethrough, said microcolumns extending from the top to the bottom surface of the microcolumn layer and optionally containing an affinity chromatography agent;
a top capping layer proximately disposed at the top surface of the microcolumn layer and comprising a patterned grid having at least one opening in fluid alignment with at least one microcolumn so as to allow a sample liquid to pass through the top capping layer and into the microcolumn; and
a reconfigurable bottom capping layer proximately disposed at the bottom surface of the microcolumn layer, said reconfigurable bottom capping layer being reconfigurable to conduct affinity chromatography in multiple microcolumns in parallel, in series, or in both parallel and series simultaneously,
wherein said bottom capping layer comprises a parallel patterned grid when configured for running multiple liquid samples through the microcolumns in a parallel manner, said parallel patterned grid comprising opening portions in fluid alignment with those microcolumns through which liquid samples are desired to pass in a parallel manner,
wherein said bottom capping layer comprises a series patterned grid when configured for passing a single liquid sample through multiple serially connected microcolumns in a serial manner, said series patterned grid further comprising a bottom channel layer having a plurality of horizontal channel portions each forming a flow channel fluidly connecting adjacent microcolumns of the serially connected microcolumns through which the single liquid sample is desired to pass in a serial manner, and
wherein said bottom capping layer comprises both said parallel patterned grid and said series patterned grid when configured for conducting said affinity chromatography in both parallel and series simultaneously.

2. The device according to claim 1, wherein the microcolumn layer is made of a material selected from the group consisting of poly(methyl methacrylate) (PMMA), cyclic olefin copolymer, polyethylene, polypropylene, and polystyrene, or functional derivatives or variants thereof.

3. The device according to claim 1, wherein the top capping layer and the bottom capping layer are made of a material selected from the group consisting of poly(methyl methacrylate) (PMMA), cyclic olefin copolymer, polyethylene, polypropylene, and polystyrene, or functional derivatives or variants thereof.

4. The device according to claim 1 further comprising:
a top channel layer disposed between the top capping layer and the top surface of the microcolumn layer, wherein the top channel layer comprises a plurality of horizontal channel portions each forming a flow channel fluidly connecting adjacent microcolumns of the serially connected microcolumns through which the single liquid sample is desired to pass in a serial manner.

5. The device according to claim 4, wherein the top channel layer is patterned to work in fluid and serial connection with the plurality of horizontal channel portions of the bottom capping layer so as to pass the single liquid sample through the serially connected microcolumns in a serial manner.

6. The device according to claim 4, wherein the top channel layer is made of a material selected from the group consisting of silicone and rubber, or functional derivatives or variants thereof.

7. The device according to claim 1 further comprising:
a top port layer proximately disposed on the top capping layer, said top port layer comprising one or more input port each in fluidic alignment with a corresponding microcolumn so as to effectuate introduction of a sample liquid into a desired microcolumn.

8. The device according to claim 7, wherein the top port layer further comprises at least one outlet port for expelling a liquid sample from one of the microcolumns after it passes through a plurality of serially connected microcolumns in serial manner.

9. The device according to claim 7, wherein the ports of the top port layer are NanoPorts™, connectors, and/or tubing made of a material selected from the group consisting of a polymer, a thermoplastic polymer, and polyether ether ketone (PEEK), or functional derviatves or variants thereof.

10. The device according to claim 1 further comprising:
a bottom port layer proximately disposed on the bottom capping layer, said bottom port layer comprising one or more outlet port each in fluidic alignment with a corresponding microcolumn so as to effectuate expulsion of a liquid sample from a desired microcolumn.

11. The device according to claim 10, wherein the ports of the bottom port layer are NanoPorts™, connectors, and/or tubing made of a material selected from the group consisting of a polymer, a thermoplastic polymer, and polyether ether ketone (PEEK), or functional derviatves or variants thereof.

12. The device according to claim 1 further comprising:
a top frit gasket layer and/or a bottom frit gasket layer for aiding the containment of an affinity chromatography agent within the microcolumns,
wherein said top frit gasket layer is deposited between the top surface of the microcolumn layer and the top capping layer, and
wherein the bottom frit gasket layer is deposited between the bottom surface of the microcolumn layer and the bottom capping layer.

13. The device according to claim 12, wherein the top and bottom frit gasket layers are made of a material selected from the group consisting of silicone, rubber, a plastic polymer, polytetrafluoroethylene, paper, metal, cork, felt, neoprene, nitrile rubber, and fiberglass, or functional derivatives or variants thereof.

14. The device according to claim 1 further comprising:
a top port layer proximately disposed on the top capping layer, said top port layer comprising one or more input port each in fluidic alignment with a corresponding microcolumn so as to effectuate introduction of a sample liquid into a desired microcolumn;
an optional bottom port layer proximately disposed on the bottom capping layer, said bottom port layer comprising one or more outlet port each in fluidic alignment with a corresponding microcolumn so as to effectuate expulsion of a liquid sample from a desired microcolumn; and
a top washer layer and/or a bottom washer layer for securing the ports fo the top port layer and the optional bottom port layer in alignment with their corresponding microcolumns,
wherein said top washer layer is proximately deposited at the top capping layer and comprises a plurality of openings through which the ports of the top port layer protrude, and
wherein said bottom washer layer is proximately deposited at the bottom capping layer and comprises a plurality of openings through which the ports of the optional bottom port layer protrude.

15. The device according to claim 14, wherein the top and bottom washer layers are made of a material selected from the group consisting of poly(methyl methacrylate) (PMMA), cyclic olefin copolymer, polyethylene, polypropylene, and polystyrene, or functional derivatives thereof.

16. The device according to claim 1, wherein the affinity chromatography agent is selected from the group consisting of a resin, a modified resin, and microbeads.

17. The device according to claim 1, wherein the affinity chromatography agent comprises an immobilized target molecule.

18. The device according to claim 17, wherein the immobilized target molecule is labeled.

19. The device according to claim 17, wherein the immobilized target molecule is selected from the group consisting of a whole cell, a virus, a virus particle, a protein, a modified protein, a polypeptide, a modified polypeptide, an RNA molecule, a DNA molecule, a modified DNA molecule, a polysaccharide, an amino acid, an antibiotic, a pharmaceutical agent, an organic non-pharmaceutical agent, a macromolecular complex, a carbohydrate, a lipid, a small molecule, a chemical compound, a mixture of lysed cells, and a mixture of purified, partially purified, or non-purified protein.

20. The device according to claim 17, wherein the immobilized target molecule is provided from a mixture of lysed cells, a mixture of purified, partially purified, or non-purified protein.

21. The device according to claim 1, wherein the microcolumns have a volume capacity of between about 0.5 µL and about 250 µL.

22. The device according to claim 1, wherein the affinity chromatography involves anion exchange technology, group exclusions, immobilized-metal affinity chromatography (IMAC), fusion tag protein purification, pull-down assays, or immunoprecipitations.

23. The device according to claim 1, wherein the one or more liquid sample comprises one or more test agent for running through at least one of the microcolumns to determine its affinity or lack of affinity to the affinity chromatography agent.

24. The device according to claim 23, wherein the test agent is selected from the group consisting of an aptamer, a protein, a protein complex, a modified protein, a polypeptide, a modified polypeptide, an RNA molecule, a DNA molecule, a modified DNA molecule, and a drug.

25. A system for collecting one or more liquid sample from an affinity chromatography microcolumn device, said system comprising:
a device according to claim 1;
a liquid flow mechanism for moving a liquid sample into, through, and out of a microcolumn; and
a liquid collection apparatus comprising well portions for collecting liquid samples from the microcolumns, wherein each well portion is aligned with a single corresponding microcolumn for collection of the liquid sample therefrom.

26. The system according to claim 25, wherein the liquid flow mechanism is programmable to move the liquid samples through the microcolumns at a desired flow rate, at a desired volume, for a desired amount of time, and/or for a desired time interval.

27. The system according to claim 25, wherein the liquid flow mechanism comprises a pump for either pushing or pulling the liquid sample through one or more of the microcolumns.

28. The system according to claim 27, wherein the pump controls flow rate of the liquid samples through the microcolumns.

29. The system according to claim 25, wherein the liquid collection apparatus is a microplate having a plurality of wells for collecting liquid samples from the microcolumns.

30. The system according to claim 29, wherein the microplate comprises a number of wells selected from the group consisting of 6, 12, 24, 48, 96, 384, 1536, 3456, and 9600 wells.

31. A method of collecting one or more liquid sample from an affinity chromatography microcolumn for further analysis, said method comprising:
providing a system according to claim 25;
running one or more liquid sample through the microcolumns of the device of the system in a parallel manner, a serial manner, or both a serial manner and parallel manner simultaneously under conditions effective to allow a test agent contained in the liquid sample to bind specifically to a target molecule contained in the microcolumn of the device; and
recovering from each microcolumn the test agent or test agents that bind specifically to the respective target molecules of each microcolumn device, said recovering taking place in the liquid collection apparatus.

32. The method according to claim 31, wherein the recovering step comprises:
   washing unbound and weakly bound test agents from each microcolumn; and
   eluting the test agents that specifically bind to the target molecules of each microcolumn.

33. The method according to claim 31, wherein the recovered test agents that specifically bind to the target molecules are nucleic acid aptamers comprising RNA aptamers, the method further comprising:
   performing reverse transcription amplification of the selected aptamer population.

34. The method according to claim 31 further comprising:
   purifying and sequencing the amplified aptamer population.

35. The method according to claim 34, wherein said recovering, said performing reverse transcription amplification, said purifying, and/or said sequencing are performed in one or more separate fluidic devices coupled in fluidic communication with the microcolumn devices.

36. The method according to claim 31, wherein each of said running and recovering is automated.

37. The method according to claim 31, wherein said liquid samples collected from the microcolumns are further used in analytical processes.

38. The method according to claim 37, wherein said analytical processes comprise high throughput processes, quantitative polymerase chain reaction (qPCR), UV-Visual absorption spectroscopy, fluorescence spectroscopy, nucleic acid sequencing, and mass spectrometry.

* * * * *